United States Patent [19]

Varma et al.

[11] Patent Number: 4,673,685
[45] Date of Patent: Jun. 16, 1987

[54] HYDROXIMIC ACIDS OF 7-OXABICYCLOHEPTANE SUBSTITUTED ETHERS AND THIOETHERS USEFUL IN THE TREATMENT OF THROMBOTIC DISEASE

[75] Inventors: Ravi K. Varma, Belle Mead; Eric M. Gordon, Pennington; Ligaya M. Simpkins, Allentown, all of N.J.

[73] Assignee: E. R. Squibb & Sons, Inc., Princeton, N.J.

[21] Appl. No.: 888,671

[22] Filed: Jul. 23, 1986

[51] Int. Cl.$^4$ ............... A61K 31/34; A61K 31/557; C07D 307/00
[52] U.S. Cl. .................. 514/333; 514/337; 514/469; 546/256; 546/269; 549/463
[58] Field of Search ............ 549/463; 514/469, 333, 514/337; 546/269, 256

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,242,273 | 12/1980 | Shepherd | 260/453 |
| 4,254,044 | 3/1981 | Sprague | 260/347.8 |
| 4,440,940 | 4/1984 | Shepherd | 560/19 |
| 4,474,803 | 10/1984 | Hall et al. | 424/285 |
| 4,536,513 | 8/1985 | Das et al. | 514/469 |

FOREIGN PATENT DOCUMENTS 0043292 8/1982 European Pat. Off. .
0082646 6/1983 European Pat. Off. .
2039909 8/1980 United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

Hydroximic acids of 7-oxabicycloheptane substituted ether and thioether prostaglandin analogs are provided having the structural formula

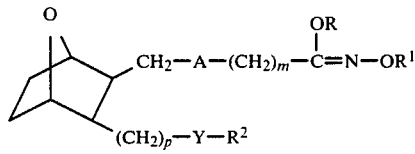

wherein Y is O or

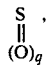

and including all stereoisomers thereof.

The compounds are inhibitors of prostaglandin and biosynthesis and as such are useful, for example, as anti-allergy and antiinflammatory agents and also as antipsoriatic agents.

24 Claims, No Drawings

HYDROXIMIC ACIDS OF 7-OXABICYCLOHEPTANE SUBSTITUTED ETHERS AND THIOETHERS USEFUL IN THE TREATMENT OF THROMBOTIC DISEASE

DESCRIPTION OF THE INVENTION

The present invention relates to hydroximic acids of 7-oxabicycloheptane substituted ethers and thioethers which are inhibitors of $\Delta^5$-lipoxygenase, inhibitors of prostaglandin and leukotriene biosynthesis and inhibitors of arachidonic acid cyclooxygenase, and as such are useful, for example, as anti-allergy and antiinflammatory and also as antisporiatic agents. These compounds have the structural formula

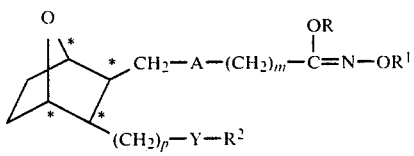

and including all stereoisomers thereof, wherein

A is $-CH=CH-$ or $-(CH_2)_2$; m is 0 to 10; R is lower alkyl, aryl, aralkyl or lower alkenyl; $R^1$ is H, lower alkyl, aryl, aralkyl, lower alkenyl, cycloalkyl, alkanoyl or aroyl; p is 1 to 5; Y is O or $S(O)_q$ wherein q is 0, 1 or 2; and $R^2$ is lower alkyl, aryl, aralkyl, cycloalkyl, cycloalkylalkyl, lower alkenyl or lower alkynyl.

Thus, the compounds of the invention include the following types of compounds:

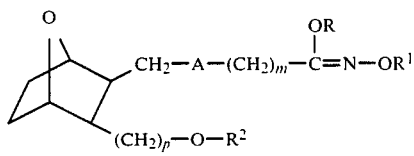 IA

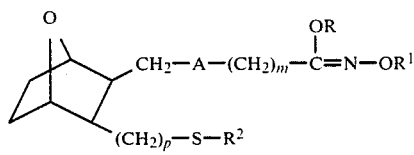 IB

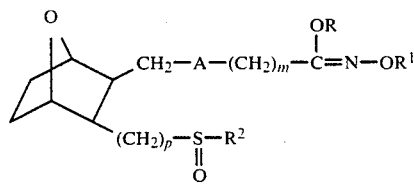 IC

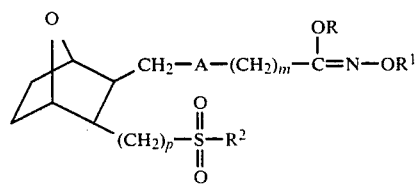 ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, a 2-, 3-, or 4-pyridyl substituent, an alkylaryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), lower alkoxy groups and/or 1 or 2 hydroxyls.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include at least one double bond in the normal chain and may contain 1 or 2 double bonds, such as 2-propenyl, 3-butenyl, 2-butenyl, 4-pentenyl, 3-pentenyl, 2-pentenyl, 2-hexenyl, 3-hexenyl, 5-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-pentynyl, 2-hexynyl, 3-hexynyl, 5-hexynyl, 2-heptynyl, 3-heptynyl, 4-heptynyl, 3-octynyl, 3-nonynyl, 4-decynyl, 3-undecynyl, 4-dodecynyl and the like.

The terms "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "$(CH_2)_m$" and "$(CH_2)_p$" include a straight or branched chain radical having 0 to 10 carbons in the normal chain in the case of "$(CH_2)_m$" and 1 to 5 carbons in the normal chain in the case of "$(CH_2)_p$" and may contain 1 or 2 lower alkyl and/or 1 or 2 halogen substituents. Examples of $(CH_2)_m$ and $(CH_2)_p$ groups include

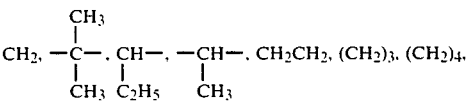

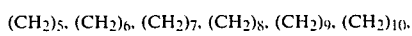

-continued

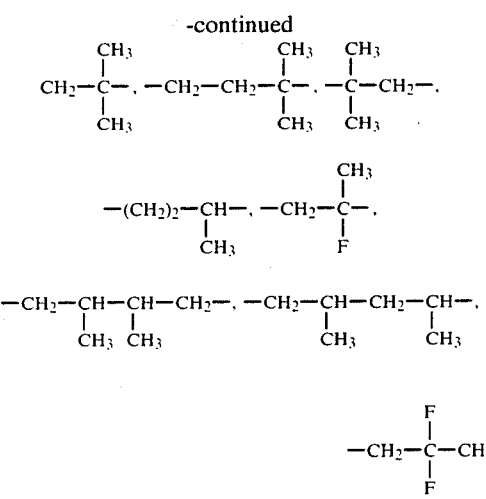

and the like.

Preferred are those compounds of formula I wherein A is —CH=CH— or —CH$_2$—CH$_2$—, m is 2 to 4, p is 1, Y is O or S, (CH$_2$)$_m$ is

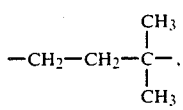

R is alkyl, as methyl, n-propyl, isopropyl, n-hexyl, or n-dodecyl, benzyl or p-fluorobenzyl, R$^1$ is H, and R$^2$ is lower alkyl, such as hexyl, aryl, such as phenyl, or aralkyl such as benzyl.

The various compounds of the invention may be prepared as outlined below.

The 7-oxabicycloheptane ether compounds of formula I of the invention wherein Y is O, p is 1, A is CH=CH and m is 0 to 10, and R$^1$ is H, that is,

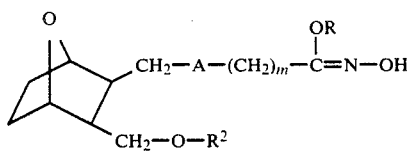

may be prepared starting with the alcohol II

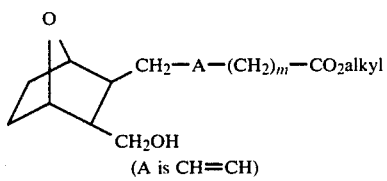

which is subjected to an ether formation reaction wherein compound II is reacted with a strong base such as KOH, NaOH or LiOH and the like in the presence of an inert solvent, such as xylene, toluene, benzene or mesitylene and sulfonate compound of the structure A Mesyl-OR$^2$ or
A' Tosyl-OR$^2$
or a halide of the structure
A'' R$^2$ Hal (Hal is Cl, Br or I) to form the ether

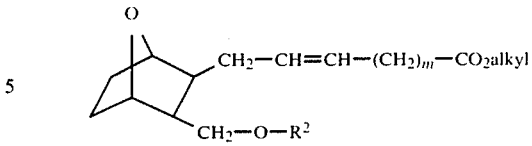

Ether III is then hydrolyzed by treating with strong base such as LiOH, KOH or NaOH to form the corresponding alkali metal salt and then neutralized with a strong acid such as HCl or oxalic acid to form IV

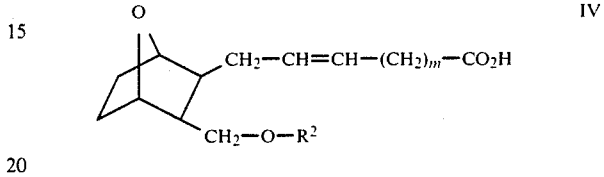

Acid IV is then subjected to hydroxamic acid formation by treating a solution of IV in an inert aromatic solvent such as benzene with oxalyl chloride and stirring the mixture at room temperature under nitrogen to form the acid chloride V

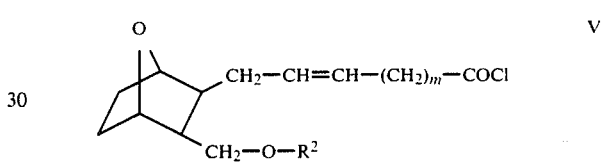

The acid chloride V is dissolved in an inert solvent such as tetrahydrofuran and added to a cold solution of hydroxylamine

H$_2$NOH in tetrahydrofuran and water in the presence of an organic base such as triethylamine. The mixture is stirred under nitrogen atmosphere while being cooled in an ice bath, to form hydroxamic acid VI.

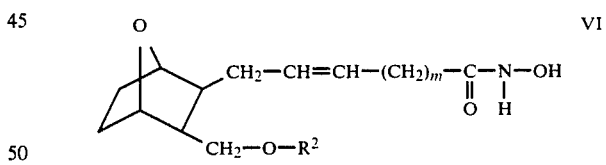

A solution of hydroxamic acid VI, 4-dimethylaminopyridine (4-DMAP) and an organic base such as triethylamine in an inert anhydrous solvent such as dichloromethane, is treated with t-butyldimethylchlorosilane at room temperature to form the hydroxyl-protected compound VII

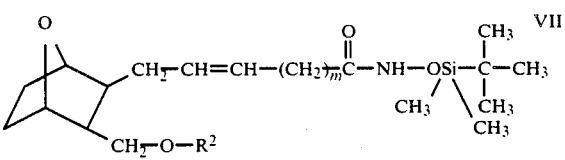

Compound VII in dry dimethylformamide or other polar solvent such as dimethyl sulfoxide or tetrahydrofuran in admixture with a cooled suspension of sodium hydride under an inert atmosphere such as nitrogen is treated with compound VIII

RX  VIII wherein X is I, Cl, F or Br, mesylate or tosylate, at reduced temperature of from about 0° to about 25° C. to form compound IX

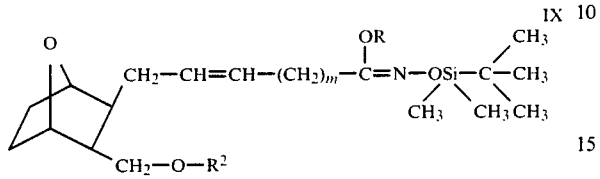   IX

Alternatively, compound IX may be formed employing a modified Mitsunobu reaction wherein compound VII is treated with diethylazodicarboxylate (DEAD), triphenylphosphine and an alcohol VIIIA

R—OH  VIIIA in the presence of an inert solvent such as tetrahydrofuran.

Compound IX is then treated with $(n-C_4H_9)_4N^{\oplus}F^{\ominus}$ in the presence of an inert solvent such as tetrahydrofuran to form compound IE.

Compounds of the invention wherein Y is O, p is 1, A is CH=CH, m is 0 to 10 and $R^1$ is other than H may be prepared by treating acid chloride V with amine X $H_2NOR^1$  X in the presence of an organic base such as triethylamine and an inert solvent such as tetrahydrofuran, 1,2-dimethoxyethane, preferably in the presence of water to form ether XI

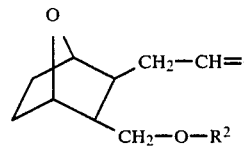   XI which is treated with sodium hydride and compound VIII to form compound of the invention IF

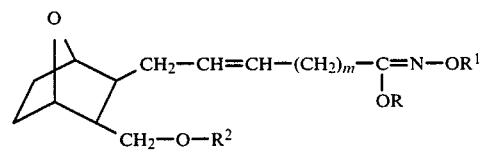   IF

Alternatively, compounds of the invention IF (wherein $R^1$=alkyl or aralkyl) may be prepared by the reaction of IE (where $R^1$=H) with an inorganic base such as sodium hydride and compound VIII.

Compounds of the invention IF (where $R^1$=alkanoyl or aroyl) may be prepared by the reaction of IE (where $R^1$=H) with an organic acid chloride XA $R_1^1COCl$ XA (where $R_1^1$ is alkyl or aryl)
in the presence of an organic base (such as pyridine).

Compounds of the invention wherein Y is O, p is 1, A is $CH_2$—$CH_2$ and m is 0 to 10 may be prepared starting with saturated acid XII

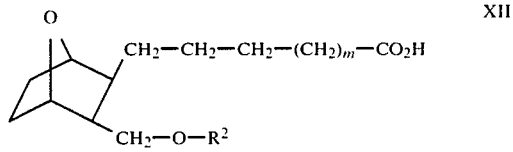   XII (prepared by hydrogenating acid IV in the presence of palladium on carbon catalyst and methanol or as described in U.S. Pat. No. 4,582,854). Acid XII is then employed in place of acid IV in the procedure outlined above with respect to the formation of compounds IE and IF to form corresponding compounds IG and IH

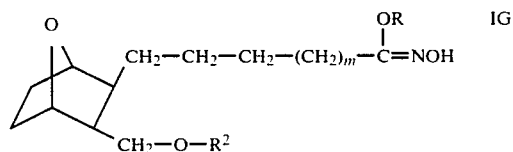   IG

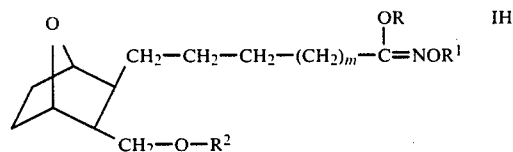   IH

Compounds of formula IG may also be prepared starting with compound IE or compound IF wherein $R^1$ is benzyl by hydrogenating IE or IF in the presence of palladium on carbon or other conventional hydrogenation catalyst and methanol to form compound IG.

Compounds of formula I wherein Y is S, A is CH=CH and p is 1, or Y is O or S, $R^2$ is benzyl, A is CH=CH or $(CH_2)_2$ and p is 1, may be prepared by starting with the hydroxymethyl compound IIA

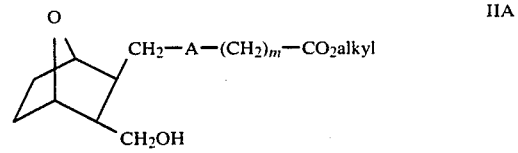   IIA and subjecting IIA to a tosylation reaction, for example, by reacting the hydroxymethyl compound IIA with tosyl chloride in pyridine and methylene chloride to form the corresponding tosylate XIII

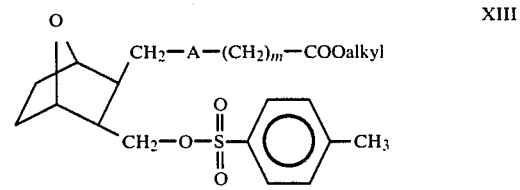   XIII

Thereafter, tosylate XIII is reacted with a thiol or mercaptan of the structure B

HSR²     B in the presence of potassium t-butoxide and a solvent such as tetrahydrofuran, dimethyl sulfoxide or dimethylformamide to form compounds of the structure XIV

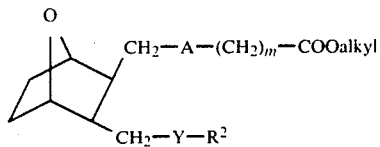

Ester XIV may then be hydrolyzed by treating with strong alkali metal base under an oxygen-free atmosphere in the presence of anti-oxidants like hydroquinone and then neutralizing with a strong acid, as described hereinbefore, to form the acid XV

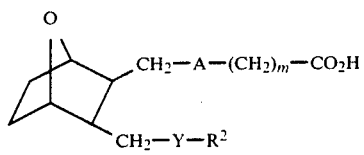

Compound XV is then subjected to hydroximic acid formation as described hereinbefore with respect to acids IV and XII to form the hydroximic acid IJ of the invention

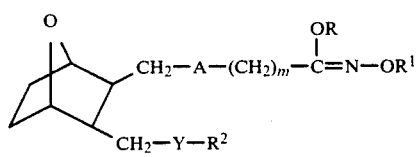

Compounds of the invention wherein p is 1, Y is S, A is CH₂—CH₂ and m is 0 to 6 may be prepared by subjecting the hydroxymethyl compound IIA to hydrogenation by treating IIA with hydrogen in the presence of a catalyst such as palladium and a solvent such as methanol to form hydroxymethyl compound IIB

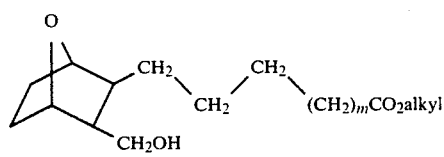

Compound IIB is then subjected to a tosylation reaction, for example, by reacting the hydroxymethyl compound with tosyl chloride in pyridine and methylene chloride to form the corresponding tosylate IIIA

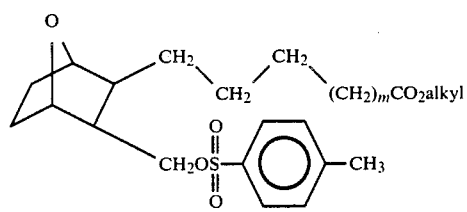

Thereafter, tosylate IIIA is reacted with a thiol or mercaptan of the structure B, above, in the presence of potassium t-butoxide and a solvent, such as tetrahydrofuran, dimethylsulfoxide, or dimethylformamide to form compounds of the invention of structure XVI

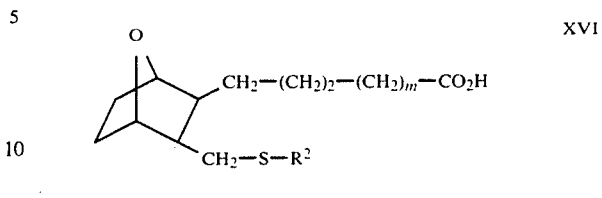

Compound XVI is then subjected to hydroximic acid formation as described hereinbefore to form hydroximic acid IK of the invention

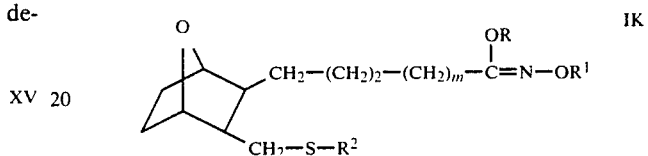

Compounds of formula I wherein p is 2 to 5 may be prepared by subjecting hydroxymethyl compound IIA (wherein A is CH=CH) or hydroxymethyl compound IIB (wherein A is —(CH₂)₂—) (formed by reducing IIA by treating with hydrogen in the presence of a palladium on carbon catalyst) to a Collins oxidation by reacting IIA or IIB with chromium trioxide-pyridine complex in the presence of a solvent such as dichloromethane to form aldehyde XVII. Aldehyde XVII

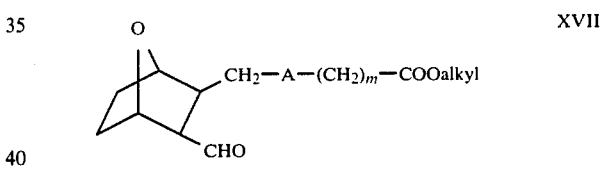

wherein A is CH=CH or CH₂—CH₂
is subjected to a homologation sequence, such as a Wittig reaction with (C₆H₅)₃P⁺Cl⁻CH₂OCH₃ followed by hydrolysis, (p−1) times, to form aldehyde XVIII

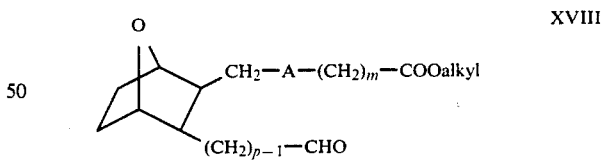

which is carried on to compounds of the invention where p is 2 to 5 by reducing aldehyde XVIII employing a reducing agent such as sodium borohydride in a solvent such as methanol to form alcohol ester XIX

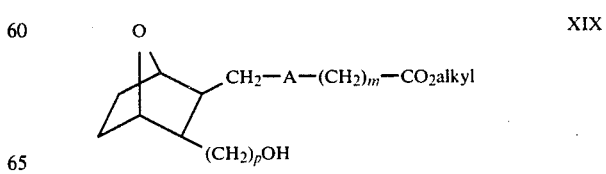

which is subjected to an etherification reaction with A, A' or A'' as described above or to a thioetherification reaction with thiol B, after conversion of XIX to its tosylate, to form XX

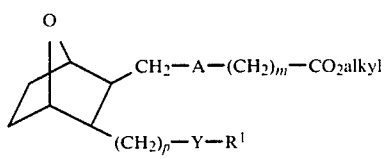   XX

Compound XX is then subjected to hydroximic acid formation as described hereinbefore to form hydroxamate IL of the invention

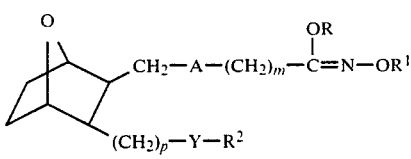   IL wherein A is CH=CH or $(CH_2)_2$, p is 2 to 5 and Y is O or S

To form compounds of formula I wherein Y is

the sulfide derivative of formula I wherein Y is S is subjected to an oxidation reaction, for example, by reacting same with 1 or 2 parts of sodium periodate, in the presence of methanol and tetrahydrofuran and water, to form the corresponding sulfinyl derivative

or sulfonyl derivative

The sulfinyl and sulfonyl derivatives may be separated from each other by chromatography or other conventional separation procedures.

The compounds of this invention where Y is O or S have four centers of asymmetry as indicated by the asterisks in formula I. Where Y is

the compounds of the invention have five centers of asymmetry. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

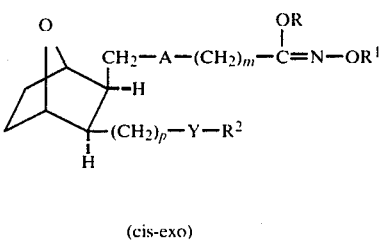   Ia (cis-exo)

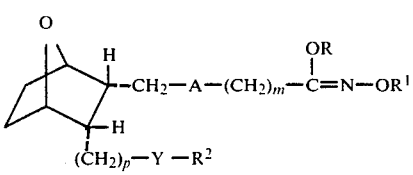   Ib (cis-endo)

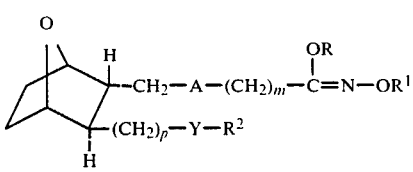   Ic (trans)

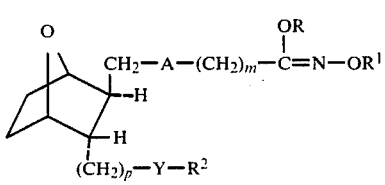   Id (trans)

The nucleus in each of the compounds of the invention is depicted as

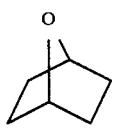

for matter of convenience; it will also be appreciated that the nucleus in the compounds of the invention may be depicted as

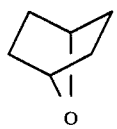

The compounds of this invention are cardiovascular agents useful as platelet aggregation inhibitors, such as inhibiting arachidonic acid-induced platelet aggregation (e.g., for treatment of thrombotic disease, such as inhibiting coronary or cerebral thromboses) and in inhibiting bronchoconstriction as induced by asthma.

They are also selective thromboxane $A_2$ receptor antagonists, e.g., having a vasodilatory effect for treatment of myocardial ischemic disease, such as angina pectoris.

The compounds of the invention are also thromboxane synthetase inhibitors and thus may also be used for preventing gastrointestinal ulcer formation. They also increase the amount of endogenous prostacyclin $PGD_2$ and therefore may be used for controlling tumor cell metastasis or as antihypertensive agents.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling, tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

In addition, the compounds of the invention are $\Delta^5$-lipoxygenase inhibitors and prevent prostaglandin and leukotriene $C_4$ formation in macrophages (Sameulsson, B., Science, Vol. 220, p. 568-575, 1983). The administration of compounds of this invention to humans or animals provides a method for treating allergy of a reagin or non-reagin nature. Asthma is preferably treated but any allergy within leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compounds of the invention are useful as antipsoriatic agents.

The compounds of the invention as well as the acid precursors thereof are useful as antiinflammatory agents in the manner of indomethacin and phenylbutazone as indicated by carragenin-induced edema in the rat [Ref: Winter et al, J. Pharmacol, Exp. Ther. 141:369, 1963] and they may be used to decrease joint swelling, tenderness, pain and stiffness in conditions such as rheumatoid arthritis.

The compounds of the invention may also be employed for treating sunburn.

An effective but essentially non-toxic quantity of the compound is employed in treatment.

The compounds of the invention can be administered orally, topically or parenterally to various mammalian species known to be subject to such maladies, e.g., humans, cattle, horses, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, cream, lotion, ointment or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, phenylmethyl ester

A.
[3aR-[1-(1R,2S,5R),3aα,4α,7α,7aα]]Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No. 4,143,054 (21 g, 0.13 mole), levo-menthol (21 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10n g of [3aR-[1-(1R,2S,5R),3aα,4α,7α,7aα]]-octahydro-1-[[5-methyl-2-(1-methylethyl)cyclohexyl]oxy]-4,7-epoxyisobenzofuran, m.p. 109°-111° C.

B.
[3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f=0.25$; vanillin spray and heat.

C.
[3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[\alpha]_D = -44°$ $[\alpha]^{Hg}_{365} = 122°$ c=10 mg/ml MeOH

TLC: silica gel, ethyl acetate/dichloromethane (1:1), $R_f=0.2$; vanillin spray and heat.

D.
[1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title D compound, b.p. 90° C./0.01 mm.

$[\alpha]_D = +44°$ $[\alpha]^{Hg}_{365} = +138°$ c=11 mg/ml MeOH

TLC: silica gel; ethyl acetate/dichloromethane (1:1); $R_f=0.2$; vanillin spray and heat.

E.
[4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°–105° C.

$[\alpha]_D = +27.2°$ $[\alpha]^{Hg}_{365} = 0°$, (c=7.9 mg/ml MeOH)

F.
[1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$ $[\alpha]^{Hg}_{365} = 0°$, (c=16.9 mg/ml MeOH)

TLC: silica gel; ether; $R_f=0.4$; vanillin spray and heat.

G.
[1R-]1α,2β(5Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was stirred and heated to reflux under argon atmosphere and 12 ml of xylene was removed by distillation. To this stirred mixture was added simultaneously a solution of 500 mg (1.86 mmol) of title F alcohol methyl ester in 16 ml of dry xylene and a solution of 1.68 g (9.30 mmol) of hexylmesylate in 16 ml of dry xylene. This mixture containing a jelly-like solid was refluxed for 1 hour and 15 minutes. The cooled reaction mixture was diluted with 100 ml of saturated NaHCO$_3$ solution and extracted with CH$_2$Cl$_2$ (3×100 ml). The combined CH$_2$Cl$_2$ extracts were washed with brine (1×200 ml), dried (MgSO$_4$), filtered and concentrated in vacuo. Purification was effected by flash chromatography on 46 g of silica gel 60 using hexane:ether (5:1) as eluant. This gave 0.62 g of title hexyl ester (79%) as a colorless oil. TLC: silica gel, 2% CH$_3$OH/CH$_2$Cl$_2$, $R_f$: 0.80, iodine.

H.
1R-[1α,2β(5Z),3β,4α]]-7-[3-[(Hexyloxy)methyl]-7-oxabicyclo[2.2.1]hept-2-yl]-5-heptenoic acid To a stirred solution of 517 mg (1.12 mmol) of Part G hexyl ester, 55 ml of distilled THF, 4.40 ml of CH$_3$OH and 7.20 ml of H$_2$O under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4×150 ml). The combined EtOAc extracts were dried (MgSO$_4$), filtered and concentrated in vacuo. The residue was chromatographed on 40 g of silica gel 60 using Et$_2$O:hexane (1:4, 1:1) and Et$_2$O as eluants to give the desired product contaminated with a small amount of hexyl alcohol. The product was pumped under high vacuum for ~60 hours at room temperature to give 350 mg (85%) of pure title acid. TLC: silica gel, 4% CH$_3$OH/CH$_2$CL$_2$, $R_f=0.42$, iodine.

$[\alpha]_D = +5.2°$ (CHCl$_3$)

Anal Calcd for C$_{20}$H$_{34}$O$_4$: C, 70.92; H, 10.12; Found: C, 70.66; H, 9.99.

I.
[1R-[1α,2β(5Z),3β,4α]]-7-[3-[(Hexyloxy)methyl]-7-oxabicyclo[2.2.1]hept-2-yl]-5-heptenoic acid, methyl ester

[1R-[1α,2α(Z),3β,4α]]-7-[3-[(Hexyloxy)methyl]-7-oxabicyclo[2.2.1]hept-2-yl]-5-heptenoic acid (1.35 g, 4 mmole, prepared as described in Parts G and H) was dissolved in Et$_2$O (~30 ml) and a moderate excess of a solution of diazomethane in Et$_2$O was added. After 5 minutes, the excess diazomethane was destroyed by the addition of 2-3 drops of glacial acetic acid. After evaporation of the solvent the residue was flash-chromatographed on a column of silica gel (LP-1, 40 g) eluting the column with ether-hexane (15:85), with tlc monitoring of the fractions, to isolate slightly impure title ester (430 mg, 31%) and pure title ester (958 mg, 68%)[1] as oils with consistent IR, H$^1$-NMR and C$^{13}$-NMR spectra and [α]$_D^{25}$ +5.47° (C, 2.01; CHCl$_3$). The total yield was 99%.

Anal Calcd for C$_{21}$H$_{36}$O$_4$: C, 71.55; H, 10.29; Found: C, 71.29; H, 10.37

[1]. The H$^1$-NMR spectrum showed the presence of 3.5 to 4% of the trans-double bond isomer.

J.
[1R-[1α,2β(2(R,S),5Z),3β,4α]]-7-[3-[(Hexyloxy)methyl]-7-oxabicyclo[2.2.1]hept-2-yl]-2-methyl-5-heptenoic acid, methyl ester A solution of diisopropylamine (4.0 mmole, 404 mg) in dry THF (75 ml) was cooled and stirred in a bath at −78° (dry ice-acetone) under nitrogen and 1.75M butyllithium in hexane (3.0 mmole, 1.8 ml) was added. After 5 minutes, a solution of the Example I ester (3.0 mmole, 1.05 g) in dry THF (12 ml) was added dropwise in the course of 5 minutes. After another 15 minutes, purified methyl iodide (neat, 12 mmole, 1.8 g) and a solution of dry hexamethyl phosphoric triamide (0.5 ml) in dry THF (1.0 ml) were added. After 1.5 hours, the solution was poured into saturated brine (150 ml) containing concentrated hydrochloric acid (2.0 ml) and was extracted with ether (3×80 ml). The extracts were combined, washed with water, dried (MgSO$_4$ anhydrous) and evaporated to afford the crude product as an oil (1.0 g). On the basis of tlc, this was a mixture of essentially two compounds: title ester (major), and Example I ester (minor). In addition, minor, more polar impurities were present. This was subjected to a flash chromatography on a silica gel (LPS-1) column to isolate title ester (950 mg, 87%).

K.
[1R-[1α,2β(5Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (dry ice-acetone) under an atmosphere of nitrogen and 1.7M n-BuLi in hexane (1.8 mmole, 1.06 ml) was added. After 5.0 minutes, a solution of [1R-[1α,2β(2(R,S),5Z),3β,4α]]-7-[3-[(hexyloxy)methyl]-7-oxabicyclo[2.2.1]hept-2-yl]-2-methyl-5-heptenoic acid, methyl ester prepared as described in Part J (1.77 mmole, 650 mg) in dry THF (6.0 ml) was added in the course of 5 minutes. After 10 minutes, purified methyl iodide (6.0 mmole, 850 mg) was added. After 1.5 hours, the solution was added into 2% hydrochloric acid (75 ml) and was extracted with ether (3×40 ml). The extracts were combined, washed with water (2×20 ml), dried (MgSO$_4$ anhydrous) and evaporated to afford impure title methyl ester as an oil (640 mg, 95%). This was subjected to a flash chromatography on a silica gel (LPS-1) column to yield title ester (630 mg). The title ester was homogeneous (tlc, Et$_2$O-hexane, 1:1) and its H$^1$ and C$^{13}$-NMR spectra were consistent with the structure.

L.
[1R-[1α,2β(5Z),3β,4α]]-7-[3-[(Hexyloxy)methyl]-7-oxabicyclo[2.2.1]hept-2-yl]-2,2-dimethyl-5-heptenoic acid A solution of Part K ester (223 mg, 0.612 mmole) in dioxane (5.0 ml) was refluxed under nitrogen with LiOH•1H$_2$O (150 mg) and water (5.0 ml) for 3.0 hours. The mixture was then acidified with concentrated HCl (to pH 2.5) diluted with brine (20 ml) and was extracted with ether (3×20 ml). The extracts were combined, washed with water (2×100 ml), dried (MgSO$_4$ anhydrous) and evaporated to afford the crude product as an oil (210 mg). This was subjected to a column chromatography on silica gel (Baker, 60-200 mesh, 10 g), eluting the column with hexane and Et$_2$O-hexane mixtures (15:85, 1:3) to isolate homogeneous (tlc) title acid as an oil (200 mg, 89%), [α]$_D^{23}$=(+)1.16° (c, 2.2; CHCl$_3$), with consistent IR, mass, H$^1$- and C$^{13}$-NMR spectral data.

Anal Calcd for C$_{22}$H$_{38}$O$_4$ (MW 366.54): C, 72.08; H, 10.46; Found: C, 72.16; H, 10.37

M.
[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenamide A solution of Part L acid (300 mg; 0.82 mmol) in dry benzene (5.0 ml) was treated with oxalyl chloride (0.5 ml; 5.51 mmole) and a solution of dry dimethyl formamide (0.05 ml) in benzene (0.2 ml) and stirred at room temperature under nitrogen for 2 hours. The excess oxalyl chloride and solvent were blown off by a stream of nitrogen while heating the reaction flask in a warm water bath and the oil obtained dried in vacuo (oil pump) for 1 hour. The residual acid chloride was dissolved in dry tetrahydrofuran (2 ml) and was added into a stirred solution of hydroxylamine hydrochloride (77 mg; 1.1 mmole) and triethylamine (0.41 ml; 3 mmole) in 75% tetrahydrofuran (5 ml) in an ice bath. After 10 minutes, the mixture was diluted with ether (50 ml ), washed successively with 5% hydrochloric acid (15 ml) and brine (2×10 ml), dried (MgSO$_4$ anhydrous) and evaporated to afford an oil. A tlc examination (silica gel; 5:95 CH$_3$OH-CH$_3$) showed the presence of a single component more polar than the starting acid. It was dried in vacuo to afford the analytical specimen as a colorless oil (200 mg, 97.1%), [α]$_D^{23}$=(−)0.95° (c, 4.7; CHCl$_3$), with consistent mass, IR (1647 cm$^{-1}$, strong, C=O; 3279 cm$^{-1}$, strong, NH, OH).

Anal Calcd for C$_{22}$H$_{39}$NO$_4$: C, 69.25; H, 10.30; N, 3.67; Found: C, 69.14; H, 10.21; N, 3.71

N.
[1R-[1α,2β(5Z),3β,4α]]-7-[3-[(Hexyloxy)methyl]-7-oxabicyclo[2.2.1]hept-2-yl]-N-[[dimethy)-(1,1-dimethylethyl)silyl]oxy]-2,2-dimethyl-5-heptanamide A solution of Part M compound (1.15 g, 2.73 mmole), 4-dimethylaminopyridine (33.2 mg, 0.27 mmole) and triethylamine (1.51 ml, 10.9 mmole) in dry dichloromethane (55 ml) was stirred under N₂ for 15 minutes, treated with t-butyldimethylchlorosilane (533.8 mg, 3.52 mmole) and stirred at room temperature for 24 hours. The mixture was diluted with dichloromethane (275 ml) and washed with water (54 ml) containing acetic acid (1.5 ml), back-extracting the aqueous wash with dichloromethane (125 ml). The combined organic extracts were washed with 5% NaHCO₃ (70 ml) and brine (70 ml), dried (anhydrous MgSO₄), filtered and evaporated to dryness. The crude product was chromatographed on a silica gel column (Baker, 60-20-0mesh, 100 ml) to give title compound as a homogeneous (TLC) oil (1.18 g, 87.4%) with consistent H¹-NMR and C¹³-NMR spectra.

O.
[1R-[1α,2β(5Z),3β,4α]]-7-[3-[(Hexyloxy)methyl]-7-oxabicyclo[2.2.1]hept-2-yl]-N-[[(dimethyl)(1,1-dimethylethyl)silyl]oxy]-2,2-dimethyl-5-heptenimidic acid, phenylmethyl ester A solution of Part N compound (400 mg, 0.81 mmole, IR: 3235 (cm⁻¹) (S), 1649 (cm⁻¹) (S) (neat)) in dry dimethylformamide (6.3 ml) was added to a cooled (0°, ice-bath) suspension of 50% NaH (42.4 mg, 0.88 mmole or 1.09 eq.) in dry dimethylformamide (6.3 ml), stirred under nitrogen for 30 minutes and treated with benzyl bromide (0.4 ml, 3.24 mmole or 4 eq.). The mixture was stirred at 0° for 30 minutes and at room temperature for 20 hours, diluted with water (25 ml) and extracted with ether (3×100 ml). The combined organic extracts were washed with brine (25 ml), dried (anhydrous MgSO₄), filtered and evaporated to dryness. The crude product contained the desired compound and a trace of slightly more polar impurity and was chromatographed on a silica gel column (Baker, 60–200 mesh, 75 ml), eluting the column with Et₂O:hexane mixtures (1:9, 1:4) to give the title compound as a homogeneous (TLC) oil (442.7 mg, 93.3%) with a consistent H¹-NMR spectrum.

P. [1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, phenylmethyl ester A solution of Part O compound (442.7 mg, 0.76 mmole) in dry tetrahydrofuran (8 ml) was mixed with Bu₄⁺NF⁻•3H₂O (735 mg, 2.28 mmole or 3 eq.) and stirred at room temperature for 41 hours under argon. The mixture was diluted with water (25 ml) and extracted with ether (4×75 ml). The combined organic extracts were washed with brine (25 ml), dried (anhydrous MgSO₄), filtered and evaporated to dryness to give an oil containing mainly the desired product and traces of three more polar (TLC) components. The crude product was chromatographed on a silica gel column (Baker, 60–200 mesh, 100 ml) eluting the column with Et₂O:hexane mixtures (1:9; 1:4) to give title product as a homogeneous (tlc) oil (203.4 mg, 56.7%): $[\alpha]_D^{25} = -17.7°$ (c=1.37, CHCl₃) with consistent analytical, mass, IR (1646 cm⁻¹, medium, C=N; 3345 L cm⁻¹, strong, OH), H¹-NMR and C¹³-NMR spectral data.

Anal Calcd for C₂₉H₄₅NO₄: C, 73.85; H, 9.62; N, 2.97; Found: C, 73.69; H, 9.59; N, 2.71

EXAMPLE 2

[1R-[1α,2β(5Z),3β,4α]]-N-[7-[3-[(Hexyloxy)methyl]-7-oxabicyclo[2.2.1]hept-2-yl]-1-methoxy-2,2-dimethyl-5-heptenylidene]hydroxylamine A. [1R-[1α,2β(5Z),3β,4α]]-N-7-[3-[(Hexyloxy)methyl]-7-oxabicyclo[2.2.1]hept-2-yl]-N-[[(dimethyl)(1,1-dimethylethyl)silyl]oxy]-2,2-dimethyl-5-heptenimidic acid, methyl ester A solution of Example 1 part N compound (496 mg, 1.0 mmole) in dry DMF (15 ml) was stirred in an ice bath under nitrogen with 50% NaH-paraffin (49 mg, 1.1 mmole) for 1.0 hour. Methyl iodide (0.275 ml, 4.0 mmole, filtered through a short column of basic alumina) was added and the solution was stirred at room temperature for 24 hours. The mixture was then diluted with brine (50 ml) and extracted with ether (3×30 ml). The extracts were combined, washed with water, dried (MgSO₄ anhydrous) and evaporated to afford the product as an oil. A tlc examination of this showed the presence of two compounds, one less polar and one more polar than Example 1, Part N compound. The mixture was chromatographed on a column of silica gel (Baker 60–200 mesh, 30 g) eluting the column with hexane and Et₂O-hexane mixtures (5:95, 1:9, 1:4 and 3:7) to isolate the N-alkylation product [1R-[1α, 2β(5Z),3β,4α]]-7-[3-[(hexyloxy)methyl]-7-oxabicyclo[2.2.1]-hept-2-yl-N-[[(dimethyl)(1,1-dimethylethyl)]silyl]oxy]-N,2,2-trimethyl-5-heptenamide (230 mg, 45.1%) and title compound (253 mg, 49.7%) as homogeneous (tlc) oils with consistent H¹ and C¹³-NMR spectral data.

B. [1R-[1α,2β(5Z),3β,4α]]-N-[7-[3-[(Hexyloxy)methyl]-7-oxabicyclo[2.2.1-]hept-2-yl]-1-methoxy-2,2-dimethyl-5-heptenylidene]-hydroxylamine A solution of Part A compound (253 mg, 0.496 mmole) in dry THF (4.0 ml) was mixed with a 1.0M solution of N-tetrabutyl ammonium fluoride in tetrahydrofuran (2.0 mmole, 1.0 ml) in an ice bath under nitrogen and was stirred at ambient temperature for 20 hours. The mixture was then diluted with water (30 ml) and extracted with ether (3×30 ml). The extracts were combined, washed with dilute brine, dried (MgSO₄ anhydrous) and evaporated to afford the crude product as an oil. A tlc examination of this revealed the presence of one product more polar than Part A compound. It was chromatographed on a column of silica gel (20 g, Baker 60–200 mesh) eluting the column with hexane and Et₂O-hexane mixtures (1:9, 15:85 and 1:4) to afford, after drying in vacuo, the analytical specimen of title product as a colorless oil (174 mg, 88%): $[\alpha]_D = (-)5.67°$ (c, 10.4; Et₂O), with consistent mass, IR (3359 cm⁻¹, strong, —OH; 1651 cm⁻¹, medium, C=N), H¹-NMR and C¹³-NMR spectral data.

Anal calcd for C₂₃H₄₁NO₄: C, 69.83; H, 10.45; N, 3.54; Found: C, 70.01; H, 10.49; N, 3.49

EXAMPLE 3

[1R-[1α,2β(5Z),3β,4α]]-N-[7-[3-[(Hexyloxy)methyl]-7-oxabicyclo[2.2.1]hept-2-yl]-2,2-dimethyl-1-propoxy-5-heptenylidene]hydroxylamine Following the procedure of Example 2 employing Example 1 Part N compound (496 mg, 1.0 mmole) and using n-C$_3$H$_7$I instead of CH$_3$I for alkylation followed by desilylation with N-tetrabutyl ammonium fluoride and chromatography gave the analytical specimen of the title product as a homogeneous (tlc) oil (335 mg, 88%), [α]$_D$=(−)5.47° (c, 14.2; Et$_2$O), with consistent mass, IR (3351 cm$^{-1}$, medium, —OH; 1653 cm$^{-1}$, medium, C—N), H$^1$-NMR and C$_{13}$-NMR spectral data.

Anal Calcd for C$_{25}$H$_{45}$NO$_4$: C, 70.88; H, 10.71; N, 3.31; Found: C, 70.93; H, 10.84; N, 3.22

EXAMPLE 4

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, 1-methylethyl ester

A. [1R-[1α,2β(5Z),3β,4α]]-7-[3-[(Hexyloxy)methyl]-7-oxabicyclo[2.2.1]hept-2-yl]-N-[[(dimethyl)(1,1-dimethylethyl)silyl]oxy]-2,2-dimethyl-5-heptenimidic acid, 1-methylethyl ester To a chilled (0°, ice bath) and stirred suspension of 50% sodium hydride-paraffin (53 mg, 1.1 mmole) in 7 ml of dry dimethylformamide under an atmosphere of nitrogen was added a solution of Example 1 Part N compound (496 mg, 1.0 mmole) in 7 ml of dry dimethylformamide. After one hour at 0°, 2-iodopropane (0.4 ml, 4 mmole, filtered through a short column of basic alumina) was added dropwise and the solution was gradually warmed up to room temperature. After 18 hours, the resulting solution was diluted with water (40 ml) and extracted with ethyl ether (3×75 ml). The combined ether extracts were washed with brine, dried over anhydrous MgSO$_4$, filtered and evaporated in vacuo to give an oil. This was chromatographed on a column of silica gel (100 g, Baker 60–200 mesh) eluting with ethyl ether-hexane (1:9 and 1:1) to give 340 mg (63.2%) of title compound with consistent H$^1$-NMR and C$^{13}$-NMR spectra.

B. [1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, 1-methylethyl ester To a stirred solution of Part A compound (340 mg, 0.634 mmole) in 6 ml of dry tetrahydrofuran was added a solution of tetrabutylammonium fluoride (1.0M in tetrahydrofuran, 1.2 ml, 1.2 mmole) under an atmosphere of nitrogen. After 18 hours, the resulting solution was diluted with water (20 ml) and extracted with ethyl ether (3×50 ml). The combined ether extracts were washed with brine, dried over anhydrous MgSO$_4$, filtered and evaporated in vacuo to give an oil. This was chromatographed on a column of silica gel (60 g, Baker 60–200 mesh) eluting with ethyl ether-hexane (5:95 and 1:9) to give 175 mg (65.4%) of the tlc-homogeneous analytical specimen of title product, [α]$_D^{25}$=−16.5° (c=1.1, CHCl$_3$) with consistent mass, IR (3357 cm$^{-1}$, OH, strong; 1651 cm$^{-1}$, medium, C=N), H$^1$-NMR and C$^{13}$-NMR spectral data.

Anal calcd for C$_{25}$H$_{45}$NO$_4$: C, 70.88; H, 10.71; N, 3.31; Found: C, 70.80; H, 10.82; N, 3.26

EXAMPLE 5

[1R-1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, hexyl ester

A. [1R-[1α,2β(5Z),3β,4α]]-7-[3-[(Hexyloxy)methyl]-7-oxabicyclo[2.2.1]hept-2-yl]-N-[[(dimethyl)(1,1-dimethylethyl)silyl]oxy]-2,2-dimethyl-5-heptenimidic acid, hexyl ester A solution of Example 1 Part N compound (500 mg, 1.01 mmole) in dry dimethylformamide (7.8 ml) was added to a cooled (0°, ice bath) suspension of 50% NaH (53 mg, 1.10 mmole) in dry DMF (7.8 ml) stirred under nitrogen for 30 minutes and treated with hexyl iodide (0.60 ml, 4.04 mmole). The mixture was stirred at 0° for 30 minutes and at room temperature for 20 hours, diluted with water (30 ml) and extracted with ether (3×125 ml). The combined organic extracts were washed with brine (30 ml), dried (anhydrous MgSO$_4$), filtered and evaporated to dryness. The crude product was chromatographed on a silica gel column (Baker, 60–200 mesh, 100 ml) to give title compound as a homogeneous (TLC) oil (510 mg, 87.1%) with consistent H$^1$-NMR and C$^{13}$-NMR spectra$^1$.

B. [1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, hexyl ester A solution of Part A compound (510 mg, 0.88 mmole) in dry tetrahydrofuran (10 ml) was mixed with N-tetrabutylammonium fluoride•3H$_2$O (841.4 mg, 2.64 mmole) and stirred at room temperature for 22 hours under N$_2$. The mixture was diluted with water and extracted thrice with ether (100 ml). The combined organic extracts were washed with brine (25 ml), dried (anhydrous MgSO$_4$), filtered and evaporated to dryness to give an oil containing mainly the desired product and traces of one less polar and one more polar (tlc) component. The crude product was combined with that obtained from a previous run (on 0.11 mmole scale) and chromatographed on a silica gel column (Baker, 60–200 mesh, 100 ml). The column was eluted with hexane and Et$_2$O:hexane mixtures (1:9; 1:4) to give title product as a homogeneous (tlc) oil (267.2 mg, 60.1%), [α]$_D$=−19.2° (c=1.3; CHCl$_3$) with consistent analytical, mass, IR (1648 cm$^{-1}$, medium, C=N; 3361 cm$^{-1}$, strong, OH) H$^1$-NMR and C$^{13}$-NMR spectral data.

Anal calcd for C$_{28}$H$_{51}$NO$_4$: C, 72,21; H, 11.04; N, 3.01; Found: C, 72.21; H, 10.80; N, 2.98

EXAMPLE 6

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, dodecyl ester

A. [1R-[1α,2β(5Z),3β,4α]]-7-[3-[(Hexyloxy)methyl]-7-oxabicyclo[2.2.1]hept-2-yl]-N-[(dimethyl)-(1,1-dimethylethyl)silyl]oxy]-2,2-dimethyl-5-heptenimidic acid, dodecyl ester To a chilled (0°, ice bath) and stirred suspension of 50% sodium hydride-paraffin (53 mg, 1.1 mmole) in 7 ml of dry dimethylformamide under an atmosphere of nitrogen was added a solution of Example 1 Part N compound (496 mg, 1.0 mmole) in 7 ml of dry dimethylformamide. After one hour at 0°, 2-iodododecane (1.184 g, 4 mmole, filtered through a short column of basic alumina) was added dropwise and the solution was gradually warmed up to room temperature. After 18 hours, the mixture was diluted with water (30 ml) and extracted with ethyl ether (3×75 ml). The combined ether extracts were washed with brine, dried over anhydrous MgSO$_4$, and evaporated in vacuo to give an oil. This was chromatographed on a column of silica gel (100 g, Baker 60–200 mesh) eluting with ethyl ether-hexane (1:9 and 1:1) to give 480 mg (87.3%) of title compound with consistent H$^1$-NMR and C$^{13}$-NMR spectra.

B.

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, dodecyl ester To a stirred solution of Part A compound (480 mg, 0.87 mmole) in 6 ml of dry tetrahydrofuran was added a solution of tetrabutylammonium fluoride (1.0M in tetrahydrofuran, 1.75 ml) under an atmosphere of nitrogen. After 18 hours, the mixture was diluted with water (20 ml) and extracted with ethyl ether (3×50 ml). The combined ether extracts were washed with brine, dried (anhydrous MgSO$_4$), filtered and evaporated in vacuo to give an oil. This was chromatographed on a column of silica gel (60 g, Baker 60-200 mesh) eluting with ethyl ether-hexane (5:95 and 1:9) to give 370 mg (77.0%) of the tlc-homogeneous analytical specimen of title product, [α]$^{25}$$_D$= −14.2° (c=0.96, CHCl$_3$) with consistent mass IR (3363 cm$^{-1}$, OH, strong, 1653 cm$^{-1}$, C=N, medium), H$^1$-NMR and C$^{13}$-NMR spectral data.

Anal calcd for C$_{34}$H$_{63}$NO$_4$: C, 74.26; H, 11.55; N, 2.55; Found: C, 74.11; H, 11.31; N, 2.57

EXAMPLE 7

[1R-[1α,2β(3Z),3β,4α]]-5-[3-[(Hexyloxy)methyl]-7-oxabicyclo[2.2.1]-hept-2-yl]-N-hydroxy-3-pentenimidic acid, phenyl methyl ester

A. 3-[2-(Tetrahydropyranyl)oxy]propyl iodine

A solution of 3-iodopropanol (15 g, 80.65 mmole), dihydropyran (14.7 ml, 161.29 mmole) and pyridium p-toluenesulfonate (500 mg, 2.0 mmole) in 100 ml of dry dichloromethane was stirred at room temperature under an atmosphere of nitrogen for 2.5 hours. The resulting mixture was diluted with dichloromethane (150 ml), washed with water and saturated sodium bicarbonate solution, dried over anhydrous MgSO$_4$ and evaporated in vacuo. The residue was flash chromatographed on a silica gel (400 g, LPS-1) column, eluting with ethyl acetate-hexane (5:95) to give 20.43 g, (93.8%) of title compound as an oil with a consistent H$^1$-NMR spectrum.

B. 3-[2-(Tetrahydropyranyl)oxy]propyltriphenyl phosphonium iodide

A solution of Part A compound (20.43 g, 75.63 mmole) and triphenylphosphine (19.84 g, 75.63 mmole) in 150 ml of dry benzene was refluxed under an atmosphere of nitrogen for 24 hours. The solvent was evaporated in vacuo to give a sticky gum. This was rinsed with acetonitrile (80 ml) when a white solid precipitated out. The solid was isolated by filtration and dried over P$_2$O$_5$ at 60° C. in vacuo to give 32.8 g (81.5%) of title compound with a consistent H$^1$-NMR spectrum.

C.

[1R-[1α,2β(5Z),3β,4α]]-5-[3-(Hydroxymethyl)-7-oxabicyclo[2.2.1]hept-2-yl]-1-[(tetrahydropyranyl)oxy]-3-pentene To a chilled (−20°, CCl$_4$-dry ice bath) and stirred slurry of Part B compound (4.224 g, 9 mmole) in 40 ml of dry tetrahydrofuran was added dropwise K-t-amylate (4.03 ml, 1.74M in toluene) over 5 minutes under an atmosphere of nitrogen. The orange solution was stirred at −20° for 2.0 hours and then a solution of [4aS-(4aα,-5α,8α,8aα)]octahydro-5,8-epoxy-(1H)-benzopyranol-ol (prepared as described in U.S. Pat. No. 4,143,054) (510 mg, 3 mmole) in 10 ml of dry tetrahydrofuran was added dropwise. The solution was gradually warmed up to room temperature, stirred for 18 hours and quenched with acetaldehyde (1.5 ml). After stirring at room temperature for another 30 minutes, the mixture was diluted with 30 ml of a saturated sodium bicarbonate solution and extracted with ethyl ether (3×50 ml). The combined ether extracts were washed with brine, dried over anhydrous MgSO$_4$ and evaporated in vacuo. The residue was flash-chromatographed on a silica gel (50 g, LPS-1) column, eluting with ethyl acetate-hexane (1:1) to give the tlc-homogeneous title compound (810 g, 91.2%) as an oil with consistent H$^1$-NMR and C$^{13}$-NMR spectra.

D.

[1R-[1α,2β(3Z),3β,4α]]-5-[3-[(Hexyloxy)methyl]-7-oxabicyclo[2.2.1]hept-2-yl]-1-[(tetrahydropyranyl)oxy]-3-pentene Powdered potassium hydroxide (900 mg, 16 mmole) in 80 ml of dry xylene was refluxed under stirring in an atmosphere of nitrogen and 35–40 ml of xylene was removed by distillation. To this solution was added dropwise a mixture of Part C compound (400 mg, 1.35 mmole) and n-hexylmesylate (1.216 g, 6.75 mmole) in 25 ml of dry xylene. The mixture was refluxed for one hour and was then cooled. Water (25 ml) was added and the solution was extracted with ethyl ether (3×50 ml). The combined ether extracts were washed with brine, dried over anhydrous MgSO$_4$ and evaporated in vacuo. The residue was flash chromatographed on a silica gel (100 g, LPS-1) column eluting with ethyl acetate-hexane (5:95) to give the tlc-homogeneous title compound (455 mg, 89.4%) as an oil with a consistent H$^1$-NMR and C$^{13}$ spectra.

E.

[1R-[1α,2β(3Z),3β,4α]]-5-[3-[(Hexyloxy)methyl]-7-oxabicyclo[2.2.1]hept-2-yl]-3-pentenol A solution of Part D compound (125 mg, 0.328 mmole) and pyridium p-toluenesulfonate (91 mg, 0.361 mmole) in 5 ml of methanol was stirred at 70° (oil bath temperature) under an atmosphere of nitrogen for 1.5 hours. The methanol was mostly removed in vacuo, the residue diluted with 15 ml of water and extracted ethyl ether (3×20 ml). The combined ether extracts were washed with brine, dried (anhydrous MgSO$_4$) and evaporated in vacuo. The residue was flash chromatographed on a silica gel (50 g, LPS-1) column eluting with ethyl acetate-hexane (1:1) to give the tlc-homogeneous title compound (85 mg, 87.3%), [α]$^{25}$$_D$= +1.7° (c=2.82, CHCl$_3$), with consistent H$^1$-NMR and C$^{13}$-NMR spectra.

F.
[1R-[1α,2β(3Z),3β,4α]]-5-[3-[(Hexyloxy)methyl]-7-oxabicyclo[2.2.1]hept-2-yl]-3-pentenoic acid To a chilled (0°, ice bath) and stirred solution of Part E compound (2.5 g, 8.5 mmole) in 100 ml of acetone (reagent grade) was added dropwise Jones' reagent until the brown color persisted. After 30 minutes at 0°, the solution was quenched with isopropyl alcohol (1.0 ml) and the brown color went away. The acetone was evaporated in vacuo. The residue was diluted with brine (50 ml) and extracted with ethyl ether (4×70 ml). The combined ether extracts were dried over anhydrous MgSO$_4$, and evaporated in vacuo to give an oil. This was chromatographed on a column of silica gel (100 g, Baker 60-200 mesh) eluting successively with ethyl acetate-hexane (1:4 and 1:1) and ethyl acetate-methanol (9:1) to give 1.5 g (56.9%) of title compound as an oil with consistent H$^1$-NMR and C$^{13}$-NMR spectra.

G.
[1R-[1α,2β(3Z),3β,4α]]-5-[3-[(Hexyloxy)methyl]-7-oxabicyclo[2.2.1]hept-2-yl]-3-pentenoyl chloride To a chilled (0°, ice bath) and stirred solution of Part F compound (800 mg, 2.58 mmole) in a mixturre of dry benzene (20 ml) and dry dimethylformamide (5 drops) was added dropwise oxalyl chloride (1.1 ml, 12.61 mmole) under an atmosphere of nitrogen. After the addition was complete, the solution was stirred at room temperature for 2 hours. The solvent was evaporated by a stream of nitrogen and the residue was dried in vacuo at room temperature for 1 hour to give title compound as a gum (847 mg, 99.9%). This was unstable to moisture and was used immediately without characterization.

H.
[1R-[1α,2β(3Z),3β,4α]]-5-[3-[(Hexyloxy)methyl]-7-oxabicyclo[2.2.1]hept-2-yl]-N-hydroxy-3-heptenamide To a chilled (0°, ice bath) and stirred solution of hydroxylamine hydrochloride (537 mg, 7.73 mmole) and triethylamine (2.8 ml, 20.09 mmole) in a mixture of tetrahydrofuran (20 ml) and water (4 ml) was added dropwise a solution of Part G compound (847 mg, 2.58 mmole) in 10 ml of dry tetrahydrofuran. After 1 hour at 0°, the solution was acidified with 5% hydrochloric acid to pH 2, concentrated in vacuo to remove most of the tetrahydrofuran, diluted with 25 ml of brine and extracted with ethyl ether (3×50 ml). The combined ether extracts were dried over anhydrous MgSO$_4$ and evaporated in vacuo to give title compound (838 mg, 99.9%) as an oil with consistent H$^1$-NMR and C$^{13}$-NMR spectra.

I.
[1R-[(1α,2β(3Z),3β,4α]]-5-[3-[(Hexyloxy)methyl]-7-oxabicyclo[2.2.1]hept-2-yl]-N-[[(dimethyl)(1,1-dimethylethyl)silyl]oxy]-3-pentenamide A mixture of Part H compound (838 mg, 257 mmole), triethylamine (1.44 ml, 10.3 mmole), 4-dimethylaminopyridine (30 mg) and t-butyldimethylchlorosilane (426 mg, 2.83 mmole) in 40 ml of dry dichloromethane was stirred at room temperature under an atmosphere of nitrogen for 24 hours. The resulting mixture was diluted with dichloromethane (150 ml) and washed with water (50 ml) containing 1.5 ml of glacial acetic acid, a saturated sodium bicarbonate solution and brine, dried (anhydrous MgSO$_4$) and evaporated in vacuo to given an oil. This was chromatographed on a column of silica gel (150 g, Baker 60-200 mesh) eluting successively with ethyl ether-hexane (1:9, 1:3 and 1:1) to give in order of increasing polarity 210 mg of the disilylated compound 1 and title compound (505 mg, 44.6%) as oils with consistent H$^1$-NMR and C$^{13}$-NMR spectra.

J.
[1R-[1α,2β(3Z)3β,4α]]-5-[3-[(Hexyloxy)methyl]-7-oxabicyclo[2.2.1]hept-2-yl]-N-[[(dimethyl)(1,1-dimethylethyl)silyl]oxy]-3-pentenimidic acid, phenyl methyl ester To a chilled (0°, ice bath) and stirred suspension of 50% sodium hydride on paraffin (61 mg, 1.26 mmole) in 7 ml of dry dimethylformamide under an atmosphere of nitrogen was added a solution of Part I compound (505 mg, 1.15 mmole) in 7 ml of dry dimethylformamide. After one hour at 0° benzyl bromide (786 mg, 4.59 mmole) was added dropwise and the solution was gradually warmed up to room temperature. After 18 hours, the mixture was diluted with water (40 ml) and extracted with ethyl ether (3×75 ml). The combined ether extracts were washed with brine (50 ml), dried (anhydrous MgSO$_4$) and evaporated in vacuo to give an oil. This was chromatographed on a column of silica gel (100 g, Baker 60-200 mesh) eluting successively with ethyl ether-hexane (1:9, 1:3 and 1:1) to give in order of increasing polarity 103 mg (20.9%) of title compound with consistent H$^1$-NMR and C$^{13}$-NMR spectra and 320 mg (64.8%) of the N-alkylation product[2], with consistent H$^1$- and C$^{13}$-NMR spectra.

K.
[1R-[1α,2β(Z),3β,4α]]-5-[3-[(Hexyloxy)methyl]-7-oxabicyclo[2.2.1]hept-2-yl]-N-hydroxy-3-pentenimidic acid, phenyl methyl ester To a stirred solution of Part J compound (220 mg, 0.51 mmole) in 4 ml of dry tetrahydrofuran was added a solution of tetrabutylammonium fluoride (1.0M in tetrahydrofuran, 1.0 ml) under an atmosphere of nitrogen. After 18 hours, the mixture was diluted with water (20 ml) and extracted with ethyl ether (3×40 ml). The combined ether extracts were washed with brine, dried (anhydrous MgSO$_4$) and evaporated in vacuo to give an oil. This was chromatographed on a column of silica gel (60 g, Baker 60-200 mesh) eluting successively with ethyl ether-hexane (1:9 and 1:1) to give 135 mg (63.5%) of the tlc-homogeneous analytical specimen of title product. $[\alpha]^{25}_D = -3.0°$ (c=1.06, CHCl$_3$) with consistent mass, IR (3346 cm$^{-1}$, OH, strong, and 1661 cm$^{-1}$, C=N, strong) H$^1$-NMR and C$^{13}$-NMR spectral data.

Anal calcd for C$_{25}$H$_{37}$NO$_4$: C, 72.25; H, 8.98; N, 3.37; Found: C, 72.02; H, 8.99; N, 3.36

Part I

1. On the basis of H$^1$-NMR and C$^{13}$-NMR spectra, this compound had the following structure:

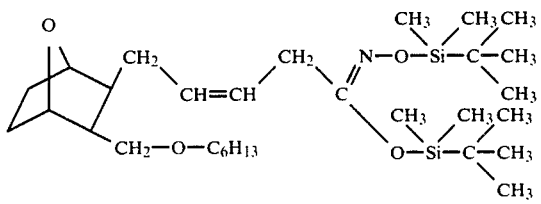

Part J

2. On the basis of $H^1$-NMR and $C^{13}$-NMR spectra, this compound had the following structure:

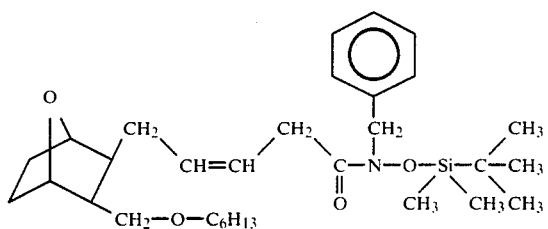

EXAMPLE 8

[1R-[1α,2β(Z),3β,4α]]-6-[3-[(Hexyloxy)methyl]-7-oxabicyclo[2.2.1]hept-2-yl]-N-hydroxy-4-hexenimidic acid, phenylmethyl ester

A.
[1R-[1α,2β(4Z),3β,4α]]-6-[3-[(Hydroxy)methyl]-7-oxabicyclo[2.2.1]hept-2-yl]-4-hexenoic acid A slurry of 3-carboxypropyltriphenylphosphonium iodide (41.13 g, 0.086 mole) and [4as-(4aα,5α,8α,8aα)]-octahydro-5,8-epoxy-(1H)-benzopyran-1-ol (10 g, 0.059 mole) in dry toluene (236 mg) was chilled to 0° (ice bath) under $N_2$ and treated dropwise with a solution of 1.74M potassium t-amylate in toluene (97.1 ml, 0.169 mole) in the course of 90 minutes. The mixture was then stirred at room temperature for 20 hours, chilled to 0° (ice-bath) and treated slowly with glacial acetic acid (9.5 ml) in toluene (11.8 ml) in the course of 30 minutes. The thick suspension was treated with water (177 ml) and brought to pH 1.5 with concentrated hydrochloric acid (12 ml). The mixture was diluted with ethyl acetate (177 ml), treated with sodium chloride (41.3 g) and stirred vigorously for 15 minutes. The resultant precipitates were removed by filtration, washing the solids with ethyl acetate (2×90 ml). The toluene-ethyl acetate layer was separated and the aqueous layer extracted with ethyl acetate (2×90 ml). The combined organic extracts were dried (anhydrous $MgSO_4$) and concentrated in vacuo to a thick oil. This oil was stirred vigorously with aqueous 5% $K_2CO_3$ (177 ml) for 30 minutes, filtered and the resultant solid washed thoroughly with water (100 ml). The aqueous filtrate was extracted with $Et_2O$:toluene (1:1, 5×59 mg), chilled in an ice bath and treated slowly with concentrated hydrochloric acid to pH 2.5. The aqueous layer was extracted with ethyl acetate (1×120 ml, 2×60 ml) and the combined extracts were dried (anhydrous $MgSO_4$), filtered and concentrated in vacuo to give title (1) compound as a thick oil (15.2 g, 100% crude yield).

B.
[1R-[1α,2β(4Z),3β,4α]]-6-[3-(Hydroxy)methyl]-7-oxabicyclo[2.2.1]hept-2-yl]-4-hexenoic acid, methyl ester A solution of Part A compound (15.2 g, 0.059 mole) in dry methanol (78 ml) was stirred vigorously with crushed amberlyst-15 resin (7.70 g) at room temperature for 2 days. The mixture was diluted with ether (80 ml) and filtered through a Celite pad, washing the pad thoroughly with ether. The combined filtrate and washings were concentrated in vacuo, the resultant oil was dissolved in ether (150 ml) and washed with 5% $NaHCO_3$ (25 ml), water (20 ml) and brine (20 ml). The organic phase was dried (anhydrous $MgSO_4$), filtered and concentrated in vacuo to a thick oil which contained the title compound as the major component and small amounts of three less polar components. This product mixture was chromatographed (gravity) on a silica gel column (Baker, 60–200 mesh, 750 ml), eluting the column with EtOAc:hexane mixtures (1:4; 1:1; 4:1) to give title compound as a homogeneous (TLC) oil (8.88 g, 61.6%).

C.
[1R-[(1α,2β(4Z),3β,4α]-6-[3-[(Hexyloxy)methyl]-7-oxabicyclo[2.2.1]hept-2-yl]-4-hexenoic acid, methyl ester A stirred suspension of crushed potassium hydroxide (18.4 g) in dry xylene (700 ml) was brought to reflux under $N_2$ and 180 ml of xylene was removed by distillation. The mixture was cooled and a solution of Part B compound (9.2 g, 0.036 mole) and n-hexylmesylate (33 g, 0.18 mole) in dry xylene (60 ml) was added. The mixture was gently refluxed, azeotroping off xylene (~180 ml) over a period of 1 hour, cooled and treated with a solution of potassium hydroxide (18.5 g, 0.33 mole) in water (220 ml). The solution was refluxed under vigorous stirring for 1.5 hours, cooled, diluted with water (450 ml) and extracted with ether (2.0 liters). The aqueous layer was acidified with concentrated hydrochloric acid (50 ml), extracted with ether (3×1.0 liters) and the combined organic extracts washed with brine (450 ml), dried (anhydrous $MgSO_4$), filtered and evaporated in vacuo to give the acid corresponding to the title compound (title B compound) as a thick oil (10.4 g, 85.6%). The crude acid was dissolved in ether (150 ml), cooled down to 0° C. (ice-bath) and treated with excess diazomethane in ether. The yellow solution was allowed to stand at 0° C. (ice-bath) for 30 minutes, at room temperature for 1 hour and the excess diazomethane blown off with a stream of nitrogen. The resulting colorless solution was evaporated in vacuo and the residual oil chromatographed on a silica gel column (Baker, 60–200 mesh, 500 ml), eluting the column with EtOAc:hexane mixtures (1:4, 1:1) to give title compound as a homogeneous oil (10.05 g, 83.5%) with a consistent $H^1$-NMR spectrum.

D.
[1R-[1α,2β(4Z),3β,4α]]-6-[3-[(Hexyloxy)methyl]-7-oxabicyclo[2.2.1]hept-2-yl]-4-hexenoic acid A solution of Part C compound (1.0 g, 2.99 mmole) and LiOH•$H_2O$ (11.96 mmole, 4 eq.) in dioxane (15 ml) and water (12 ml) was refluxed under nitrogen for 2.5 hours, cooled, brought to pH 4.0 with 12N HCl (~4.2 ml) and evaporated on a rotary evaporator to remove most of the dioxane. The slurry was diluted with brine (30 ml) and extracted with ether (3×50 ml). The combined ether extracts were washed with brine (2×15 ml), dried (anhydrous $MgSO_4$), filtered and evaporated to give title compound as a homogeneous (TLC) oil (972.5 mg, 100%) with consistent $H^1$-NMR and $C^{13}$-NMR spectral data.

E.
[1R-[1α,2β(4Z),3β,4α]]-6-[3-[(Hexyloxy)methyl]-7-oxabicyclo[2.2.1]hept-2-yl]-4-hexenoyl chloride and

[1R-[1α,2β(4Z),3β,4α]]-6-[3-[(Hexyloxy)methyl]-7-oxabicyclo[2.2.1]hept-2-yl]-N-hydroxy-4-hexenamide A solution of Part D compound (972.5 mg, 2.99 mmole) in dry benzene (15 ml) was cooled down to 0° (ice-bath) under nitrogen and treated dropwise with oxalyl chloride (3.8 ml; 43.6 mmole; 145 eq.) followed by a solution of dimethylformamide (4 drops) in dry benzene (2.5 ml). The solution was stirred at 0° for 30 minutes, at room temperature for one hour and the excess solvent and oxalyl chloride blown off with a stream of nitrogen while heating the flask in a warm water bath. The resultant acid chloride was dried in vacuo (oil pump) for 2 hours, dissolved in dry tetrahydrofuran (10 ml) and added to a cooled (0°, ice-bath) solution of hydroxylamine hydrochloride (97%; 418.5 mg) and triethylamine (2.3 ml; 16.4 mmole) in tetrahydrofuran (20.6 ml) and water (6.9 ml). The mixture was stirred at 0° (ice-bath) for 30 minutes, diluted with ether (250 ml) and washed with 5% HCl (70 ml) and brine (2×50 ml). The organic phase was dried (anhydrous MgSO4), filtered and evaporated to give title compound as a homogeneous (TLC) oil (1.09 g; 100%) with a consistent $H^1$-NMR spectrum.

F.
[1R-[1α,2β(4Z),3β,4α]]-6-[3-[(Hexyloxy)methyl]-7-oxabicyclo[2.2.1]hept-2-yl]-N-[[(dimethyl)(1,1-dimethyl)silyl]oxy]-4-hexenamide A solution of Part E compound (1.0 g, 2.99 mmole), 4-dimethylaminopyridine (38.1 mg) and Et3N (1.73 ml; 12.5 mmole) and t-butyldimethylsilyl chloride (424.6 mg, 12 mmole) in dry dichloromethane (63 ml) was stirred at room temperature under nitrogen for 20 hours. The mixture was diluted with dichloromethane (300 ml) and washed with water (60 ml) containing glacial acetic acid (1.6 ml). The aqueous phase was back-extracted with dichloromethane (135 ml) and the combined organic extracts were washed with 5% NaHCO3 (75 ml), brine (75 ml), dried (anhydrous MgSO4), filtered and evaporated to give an oil containing the title compound as the major component and traces of one less polar and three more polar components (tlc). This product mixture was chromatographed on a silica gel column (Baker, 60–200 mesh, 50 ml), eluting the column with EtOAc:hexane (1:1) and EtOAc to give title compound as a homogeneous (TLC) oil (1.24 g, 91.2%) with consistent $H^1$-NMR and $C^{13}$-NMR spectral data.

G.
[1R-[1α,2β(4Z),3β,4α]]-6-[3-[(Hexyloxy)methyl]-7-oxabicyclo[2.2.1]hept-2-yl]-N-[[(dimethyl)-(1,1-dimethyl)silyl]-oxy]-4-heptenimidic acid, phenyl methyl ester A solution of Part F compound (1.24 g, 2.73 mmole) in dry dimethylformamide (21 ml) was added to a cooled (0°, ice bath) suspension of 50% NaH (160 mg, 3.33 mole) in dry dimethylformamide (21 ml), stirred under nitrogen for 30 minutes and treated with benzyl bromide (1.34 ml, 10.9 mmoles). The mixture was stirred at 0° for 30 minutes and at room temperature for 20 hours, diluted with water (85 ml) and extracted with ether (3×300 ml). The combined organic extracts were washed with brine (85 ml), dried (anhydrous MgSO4), filtered and evaporated to dryness. The crude product contained the desired product as one of the two minor components, a major component (shown by $H^1$ and $C^{13}$ NMR spectra to be the N-benzylated isomer) and traces of three other components. This mixture was chromatographed on a silica gel column (Baker, 60–200 mesh, 150 ml), eluting the column with Et2O:hexane mixtures (1:9; 1:4) to give title compound as a homogeneous (TLC) oil (272 mg, 19%) with consistent $H^1$-NMR and $C^{13}$-NMR spectral data.

H.
[1R-[1α,2β(Z),3β,4α]]-6-[3-[(Hexyloxy)methyl]-7-oxabicyclo[2.2.1]hept-2-yl]-N-hydroxy-4-hexenimidic acid, phenylmethyl ester A solution of Part G compound (259.6 mg, 0.48 mmole) in dry tetrahydrofuran (6.0 ml) was cooled to 0° (ice bath) under nitrogen, treated with 1M Bu4NF in tetrahydrofuran (0.95 ml, mg, 0.95 mmole), warmed up to room temperature and stirred for 24 hours. The mixture was diluted with water (15 ml), extracted with ether (3×50 ml) and the combined ether extracts washed with brine (15 ml), dried (anhydrous MgSO4), filtered and evaporated to dryness to give an oil containing title product as the major component, traces of two less polar and one more polar components (TLC). This mixture was chromatographed twice on silica gel columns (Baker, 60–200 mesh), eluting the columns with Et2O:hexane mixtures (1:9, 1:4, 1:2, 1:1) to give the analytical specimen of the title product as a homogeneous (TLC) oil (110.4 mg, 53.5%): $[\alpha]_D^{25}$ +0.84° (c=1.07 CHCl3), with consistent mass IR (1659 cm$^{-1}$, strong, C=N; 3351 cm$^{-1}$, strong, —OH), $H^1$-NMR and $C^{13}$-NMR spectral data.

Anal calcd for $C_{26}H_{39}NO_4$: C, 72.69; H, 9.15; N, 3.26; Found: C, 72.56; H, 9.39; N, 3.20

EXAMPLE 9

[1R-[1α,2β(5Z),3β,4α]]-7-[3-[(Hexyloxy)methyl]-7-oxabicyclo[2.2.1]hept-2-yl]-2,2-dimethyl-N-(phenylmethoxy)-5-heptenimidic acid, 2-phenylethyl ester A. [1R-[1α,2β(5Z),3β,4α]]-7-[3-[(Hexyloxy)methyl]-7-oxabicyclo[2.2.1]hept-2-yl]-2,2-dimethyl-5-heptenoyl chloride To a chilled (0°, ice bath) and stirred solution of Example 1 Part L acid (250 mg, 0.682 mmole) in a mixture of benzene (7 ml) and dimethylformamide (3 drops) was added dropwise oxalyl chloride (0.5 ml, 5.73 mmole) under an atmosphere of nitrogen. After the addition was complete, the solution was stirred at room temperature for 1.5 hours. The solvent was evaporated by a stream of nitrogen and the gummy residue was dried in vacuo at room temperature for 1 hour to give title compound as an oil (262 mg, 99.8%). This was unstable to moisture and was used immediately without characterization.

B. [1R-[1α,2β(5Z), 3β,4α]]-7-[3-[(Hexyloxy)methyl]-7-oxabicyclo[2.2.1-]hept-2-yl]-2,2-dimethyl-N-(phenylmethoxy)-5-heptenamide To a chilled (0°, ice bath) and stirred solution of O-benzylhydroxylamine hydrochloride (1.11 g, 6.98 mmole) in a mixture of tetrahydrofuran (20 ml) and water (4 ml) was added triethylamine (3.9 ml, 27.9 mmole), followed by a solution of Part A compound (1.075 g, 2.79 mmole) in 20 ml of dry tetrahydrofuran.

After the addition was complete, the solution was stirred at room temperature under an atmosphere of nitrogen for 30 minutes. The resulting solution was acidified with 5% hydrochloric acid to pH=3, concentrated in vacuo to remove most of the tetrahydrofuran, saturated with sodium chloride and extracted with ethyl ether (4×50 ml). The combined ether extracts were washed with water, dried (anhydrous MgSO$_4$) and evaporated in vacuo to give an oil. This was chromatographed on a column of silica gel (150 g, Baker 60–200 mesh) eluting successively with ethyl ether-hexane (1:9 and 1:4) to give 1.10 g (83.5%) of the tlc-homogeneous title compound as an oil with consistent H$^1$-NMR and C$^{13}$-NMR spectra.

C.

[1R-[1α,2β(5Z),3β,4α]]-7-[3-[(Hexyloxy)methyl]-7-oxabicyclo[2.2.1]hept-2-yl]-2,2-dimethyl-N-(phenylmethoxy)-5-heptenimidic acid, 2-phenylethyl ester To a chilled (0°, ice bath) and stirred solution of Part B compound (157 mg, 0.33 mmole), triphenylphosphine (111 mg, 0.425 mmole) and phenethyl alcohol (51 μl, 0.425 mmole) in dry tetrahydrofuran (1.0 ml) under an atmosphere of nitrogen was added dropwise diethyl azodicarboxylate (DEAD, 67 μl, 0.425 mmole) over 5 minutes. After 30 minutes at 0°, the reaction was allowed to warm to room temperature for 3.5 hours. The tlc of an aliquot indicated that there was present 50–60% of unreacted Part B compound. Therefore, triphenylphosphine (111 mg), phenethyl alcohol (51 μl) and DEAD (67 μl) were successively added and the mixture was stirred overnight while Part B compound disappeared (tlc). The solvent was evaporated by a stream of nitrogen. The residue was rinsed with ethyl ether-hexane (1:1, 50 ml) and filtered. The filtrate was concentrated in vacuo and chromatographed on a column of silica gel (60 g, Baker 60–200 mesh) eluting with ethyl ether-hexane (1:9) to give 150 mg (78.3%) of the tlc-homogeneous analytical specimen of title product, [α]$^{25}_D$=+1.8° (c=0.5, CHCl$_3$) with consistent mass, IR (1628 cm$^{-1}$, C=N, medium), H$^1$-NMR and C$^{13}$-NMR spectral data.

Anal calcd for C$_{37}$H$_{53}$NO$_4$: C, 77.17; H, 9.28; N, 2.43; Found: C, 76.89; H, 9.45; N, 2.28

EXAMPLE 10

[1R-[1α,2β(Z),3β,4α]]-7-[3-[(Hexyloxy)methyl]-7-oxabicyclo[2.2.1]hept-2-yl]-2,2-dimethyl-N-(phenylmethoxy)-5-heptenimidic acid, phenyl methyl ester Example 9, Part D compound was reacted with benzyl bromide and sodium hydride in dimethyl formamide as described in Example 1, Part O, to give the title product. The title product is a colorless homogeneous (tlc) oil, [α]$^{25}_D$=(+)0.083° (c, 6.0; Et$_2$O) with consistent mass, IR (1627 cm$^{-1}$, medium, C=N), H$^1$-NMR and C$_{13}$-NMR spectral data.

Anal calcd for C$_{36}$H$_{51}$NO$_4$: C, 76.96; H, 9.15; N, 2.49; Found: C, 76.83; H, 9.23; N, 2.39

EXAMPLE 11

[1R-[1α,2β(5Z), 3β,4α]]-7-[3-[(Hexyloxy)methyl]-7-oxabicyclo[2.2.1]hept-2-yl]-N-hydroxy-2,2-dimethyl-5-heptenimidic acid, 2-phenylethyl ester

A.

[1R-[1α,2β(5Z),3β,4α]]-7-[3-[(Hexyloxy)methyl]-7-oxabicyclo[2.2.1]hept-2-yl]-N-[[(dimethyl)-(1,1-dimethyl)silyl[oxy]-2,2-dimethyl-5-heptenimide acid, 2-phenylethyl ester To a chilled (0°, ice bath) and stirred solution of Example 1 Part N compound (415 mg, 0.84 mmole), triphenylphosphine (275 mg, 1.05 mmole) and phenethyl alcohol (125 μl, 1.05 mmole) in dry tetrahydrofuran (4 ml) under an atmosphere of nitrogen was added dropwise diethyl azodicarboxylate (DEAD, 165 μl, 1.05 mmole) over 5 minutes. After 30 minutes at 0°, the reaction was allowed to warm to room temperature for another 4 hours. The solvent was evaporated by a stream of nitrogen. The residue was rinsed with ethyl ether-hexane (1:4) and filtered. The filtrate was concentrated in vacuo and chromatographed on a column of silica gel (150 g, Baker 60–200 mesh) eluting with Et$_2$O-hexane 5:95) to give 385 mg (76.7%) of title compound as an oil with consistent H$^1$-NMR and C$^{13}$-NMR specta.

B. [1R-[1α,2β(5Z), 3β,4α]]-7-[3-[(Hexyloxy)methyl]-7-oxabicyclo[2.2.1]hept-2-yl]-N-hydroxy-2,2-dimethyl-5-heptenimidic acid, 2-phenylethyl ester To a stirred solution of Part A compound (385 mg, 0.642 mmole) in 5 ml of dry tetrahydrofuran was added a solution of tetrabutylammonium fluoride (1.0 M in tetrahydrofuran, 0.95 ml) under an atmosphere of nitrogen. After 18 hours, the mixture was diluted with water (25 ml) and extracted with ethyl ether (4×30 ml). The combined ether extracts were washed with brine, dried (anhydrous MgSO$_4$), filtered and evaporated in vacuo to give an oil. This was chromatographed on a column of silica gel (80 g, Baker 60–200 mesh) eluting successively with ethyl ether-hexane (1:9 and 1:4) to give 280 mg (89.8%) of the tlc-homogeneous analytical specimen of title product, [α]$^{25}_D$= −22.9° (c=0.77, CHCl$_3$) as an oil with consistent mass, IR (3350 cm$^{-1}$, OH, strong; 1652 cm$^{-1}$, C=N, medium), H$^1$-NMR and C$^{13}$-NMR spectral data.

Anal calcd for C$_{30}$H$_{47}$NO$_4$: C, 74.18; H, 9.76; N, 2.88; Found: C, 74.01; H, 9.75; N, 2.85

EXAMPLE 12

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, 2-propenyl ester

A.

[1R-[1α,2β(5Z),3β,4α]]-7-[3-[(Hexyloxy)methyl]-7-oxabicyclo[2.2.1]hept-2-yl]-N-[[dimethyl)-(1,1-dimethylethyl)silyl]oxy]-2,2-dimethyl-5-heptenimide acid, 2-propenyl ester To a chilled (0°, ice bath) and stirred solution of 50% sodium hydride in paraffin (53 mg, 1.1 mmole) in 2.5 ml of dry dimethylformamide under an atmosphere of nitrogen was added a solution of Example 1 Part N compound (496 mg, 1.0 mmole), in 2.5 ml of dry dimethylformamide. After 1.5 hours at 0°, allyl bromide (0.35 ml, 4 mmole, filtered through a short column of basic alumina) was added dropwise and the solution was gradually warmed to room temperature. After 18 hours, the mixture was diluted with water (20 ml) and extracted with ethyl ether (4×30 ml). The combined ether extracts were washed with brine, dried over anhydrous MgSO$_4$ and evaporated in vacuo to give an oil. A tlc examination (silica gel, EtOAc-hexane 1:4) showed one major less polar spot and 4 other minor components. This was chromatographed on a column of silica gel (150 g, Baker 60–200 mesh) eluting with ethyl ether-hexane (5:95) to give 368 mg (68.7%) of title compound with consistent H$^1$-NMR and C$^{13}$-NMR spectra.

B.
[1R-[1α,2β(Z),3β,4α]]-7-[3-[(Hexyloxy)methyl]-7-oxabicyclo[2.2.1]hept-2-yl]-N-hydroxy-2,2-dimethyl-5-heptenimidic acid, 2-propenyl ester To a stirred solution of Part A compound (368 mg, 0.687 mmole), in dry tetrahydrofuran was added a solution of tetrabutylammonium fluoride (1.0M in tetrahydrofuran, 1.4 ml. 1.4 mmole) under an atmosphere of nitrogen. After 18 hours, the mixture was diluted with water (20 ml) and extracted with ethyl ether (4×30 ml). The combined ether extracts were washed with brine, dried (anhydrous MgSO$_4$), filtered and evaporated in vacuo to give an oil. This was chromatographed on a column of silica gel (100 g, Baker 60–200 mesh) eluting with ethyl ether-hexane (1:4) to give 265 mg (91.5%) of the tlc-homogeneous analytical specimen of title product, [α]$_D^{25}$ = −20.3° (c=0.69, CHCl$_3$) with consistent mass, IR (3345 cm$^{-1}$, OH, strong; 1647 cm$^{-1}$, C=N, medium), H$^1$-NMR and C$^{13}$-NMR spectral data.

Anal calcd for C$_{25}$H$_{43}$NO$_4$: C, 71.22; H, 10.28; N, 3.32; Found: C, 71.40; H, 10.42; N, 3.49

EXAMPLE 13
[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, (4-fluorophenyl)methyl ester

A.
[1R-[1α,2β(5Z),3β,4α]]-7-[3-[(Hexyloxy)methyl]-7-oxabicyclo[2.2.1]hept-2-yl]-N-[[(dimethyl)-(1,1-dimethylethyl)silyl]oxy]-2,2-dimethyl-5-heptenimidic acid, (4-fluorophenyl)methyl ester To a chilled (0°, ice bath) and stirred suspension of 50% sodium hydride-paraffin (53 mg, 1.1 mmole) in 2.5 ml of dry dimethylformamide under an atmosphere of nitrogen was added a solution of Example 1 Part N compound (496 mg, 1.0 mmole), in 2.5 ml of dry dimethylformamide. After 1.5 hours at 0°, 4-fluorobennzyl bromide (498 mg, 4 mmole) was added dropwise and the solution was gradually warmed up to room temperature. After 18 hours, the resulting solution was diluted with water (30 ml) and extracted with ethyl ether (4×40 ml). The combined ether extracts were washed with brine, dried (anhydrous MgSO$_4$), filtered and evaporated in vacuo to give an oil. This was chromatographed on a column of silica gel (150 g, Baker 60–200 mesh) eluting with ethyl ether-hexane (5:95) to give 480 mg (79.5%) of title compound with consistent H$^1$-NMR and C$^{13}$-NMR spectra.

B.
[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, (4-fluorophenyl)methyl ester To a stirred solution of Part A compound (480 mg, 0.795 mmole) in 6 ml of dry tetrahydrofuran was added a solution of tetrabutylammonium fluoride (1.0M in tetrahydrofuran, 1.6 ml) under an atmosphere of nitrogen. After 18 hours, the resulting solution was diluted with water (20 ml) and extracted with ethyl ether (4×30 ml). The combined ether extracts were washed with brine, dried (anhydrous MgSO$_4$), filtered and evaporated in vacuo to give an oil. This was chromatographed on a column of silica gel (100 g, Baker 60–200 mesh) eluting with ethyl ether-hexane (1:4) to give 355 mg (91.2%) of the tlc-homogeneous analytical specimen of title product [α]$_D^{25}$ = −15.5° (c=1.85, CHCl$_3$) with consistent mass, IR (3344 cm$^{-1}$, OH, strong, 1651 cm$^{-1}$, C=N, medium), H$^1$-NMR and C$^{13}$-NMR spectral data.

Anal calcd for C$_{29}$H$_{44}$FNO$_4$: C, 71.13; H, 9.06; F, 3.88; N, 2.86; Found: C, 70.93; H. 9.10; F, 3.83; N, 2.79

EXAMPLE 14
[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, cyclohexyl ester

A.
[1R-[1α,2β(5Z),3β,4α]]-7-[3-[(Hexyloxy)methyl]-7-oxabicyclo[2.2.1]hept-2-yl]-N-[[(dimethyl)-(1,1-dimethyl)silyl]oxy]-2,2-dimethyl-5-heptenimidic acid, cyclohexyl ester To a chilled (0°, ice bath) and stirred solution of Example 1 Part N compound (496 mg, 1.0 mmole), triphenylphosphine (328 mg, 1.25 mmole) and cyclohexanol (0.13 μl, 1.25 mmole) in dry tetrahydrofuran (5 ml) under an atmosphere of nitrogen was added dropwise diethyl azodicarboxylate (DEAD, 197 μl, 1.25 mmole) over 5 minutes. After 30 minutes at 0°, the reaction was stirred at room temperature for another 4 hours. The tlc of an aliquot indicated that there was 50–60% of unreacted Example 1 Part N compound, therefore, triphenylphosphine (328 mg), cyclohexanol (0.13 ml) and DEAD (0.2 ml) were successively added and the mixture was stirred overnight while Example 1 Part N compound disappeared (tlc). The solvent was evaporated by a stream of nitrogen. The residue was rinsed with ethyl ether-hexane (1:4) and filtered. The filtrate was concentrated in vacuo and chromatographed on a column of silica gel (120 g, Baker 60–200 mesh) eluting with ethyl ether-hexane (5:95) to give 470 mg (81.3%) of title compound as an oil with consistent H$^1$-NMR and C$^{13}$-NMR spectra.

B.
[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, cyclohexyl ester To a stirred solution of Part A compound (470 mg, 0.813 mmole) in 5 ml of tetrahydrofuran was added a solution of tetrabutylammonium fluoride (1.0M in tetrahydrofuran, 1.8 ml) under an atmosphere of nitrogen. After 18 hours, the mixture was diluted with water (25 ml) and extracted with ethyl ether (4×30 ml). The combined ether extracts were washed with brine, dried (anhydrous MgSO$_4$), filtered and evaporated in vacuo to give an oil. This was chromatographed on a column of silica gel (100 g, Baker 60–200 mesh) eluting with ethyl ether-hexane (15:85) to give 300 mg (79.6%) of the tlc-homogeneous analytical specimen of title product, $[\alpha]^{25}_D = (-)19.3°$ (c=0.82, CHCl$_3$) as an oil with consistent mass, IR (3366 cm$^{-1}$, OH, strong; 1651 cm$^{-1}$, C=N, medium), H$^1$-NMR and C$^{13}$-NMR spectral data.

Anal calcd for C$_{28}$H$_{49}$NO$_4$: C, 72.52; H, 10.65; N, 3.02; Found: C, 72.57; H, 10.53; N, 2.96

EXAMPLE 15

[1R-[1α,2β(5Z),3β,4α9]-7-[3-[(Hexyloxy)methyl]-7-oxabicyclo[2.2.1]hept-2-yl]-N-hydroxy-2,2-dimethyl-5-heptenimidic acid, (4-methoxyphenyl)methyl ester

A.

[1R-[1α,2β(5Z),3β,4α]]-7-[3-[(Hexyloxy)methyl]-7-oxabicyclo[2.2.1]hept-2-yl]-N-[[(dimethyl)-(1,1-dimethylethyl)silyl]oxy]-2,2-dimethyl-5-heptenimidic acid, (4-methoxyphenyl)methyl ester To a chilled (0°, ice bath) and stirred solution of Example 1 Part N compound (496 mg, 1.0 mmole), triphenylphosphine (328 mg, 1.25 mmole) and 4-methoxybenzyl alcohol (156 μl, 1.25 mmole) in dry tetrahydrofuran (5 ml) under an atmosphere of nitrogen was added dropwise diethyl azodicarboxylate (DEAD, 197 μl, 1.05 mmole) over 5 minutes. After 30 minutes at ~0°, the reaction was stirred at room temperature for another 3 hours. The solvent was evaporated by a stream of nitrogen. The residue was rinsed with ethyl ether-hexane (1:4) and filtered. The filtrate was concentrated in vacuo and chromatographed on a column of silica gel (120 g, Baker 60-200 mesh) eluting with ethyl ether-hexane (5:95) to give 455 mg (73.8%) of the tlc-homogeneous title compound as an oil with consistent H$^1$-NMR and C$^{13}$-NMR spectra.

B.

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, (4-methoxyphenyl)methyl ester To a stirred solution of Part A compound (455 mg, 0.74 mmole) in 8 ml of tetrahydrofuran was added a solution of tetrabutylammonium fluoride (1.0 m, in tetrahydrofuran, 1.6 ml) under an atmosphere of nitrogen. After 18 hours, the mixture was diluted with water (25 ml) and extracted with ethyl ether (4×40 ml). The combined ether extracts were washed with brine, dried (anhydrous MgSO$_4$), filtered and evaporated in vacuo to give an oil. This was chromatographed on a column of silica gel (100 g, Baker 60-200 mesh) eluting with ethyl ether-hexane (1:4) to give 295 mg (79.6%) of the tlc-homogeneous analytical specimen of title product $[\alpha]^{25}_D = -18.6°$ (c=1.0, CHCl$_3$) as an oil with consistent mass, IR (3340 cm$^{-1}$, OH, strong; 1649 cm$^1$, C=N, medium), H$^1$-NMR and C$^{13}$-NMR spectral data.

Anal calcd for C$_{30}$H$_{47}$NO$_5$: C, 71.82; H, 9.44; N, 2.79; Found: C, 71.91; H, 9.55; N, 2.75

EXAMPLE 15A

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, (2-fluorophenyl)methyl ester

A.

[1R-[1α,2β(5Z),3β,4α]]-7-[3-[(Hexyloxy)methyl]-7-oxabicyclo[2.2.1]hept-2-yl]-N-[[(dimethyl)-(1,1-dimethyl)silyl]oxy]-2,2-dimethyl-5-heptenimidic acid, (2-fluorophenyl)methyl ester To a chilled (0°, ice bath) and stirred solution of Example 1 Part N compound (496 mg, 1.0 mmole), triphenylphosphine (328 mg, 1.25 mmole) and 2-fluorobenzyl alcohol (134 μl, 1.25 mmole) in dry tetrahydrofuran (5 ml) under an atmosphere of nitrogen was added dropwise diethyl azodicarboxylate (DEAD, 197 μl, 1.25 mmole) over 5 minutes. After 30 minutes at 0°, the reaction was stirred at room temperature for another 4 hours. The solvent was evaporated by a stream of nitrogen. The residue was rinsed with ethyl ether-hexane (1:4) and filtered. The filtrate was concentrated in vacuo and chromatographed on a column of silica gel (100 g, Baker 60-200 mesh) eluting with ethyl ether-hexane (5:95) to give 400 mg (66.2%) of title compound as an oil with consistent H$^1$-NMR and C$^{13}$-NMR spectra.

B.

[1R-[1α,2β(5Z),3β,4α]]-7-[3-[(Hexyloxy)methyl]-7-oxabicyclo[2.2.1]hept-2-yl]-N-hydroxy-2,2-dimethyl-5-heptenimidic acid, (2-fluorophenyl)methyl ester To a stirred solution of Part A compound (400 g, 0.66 mmole) in 5 ml of tetrahydrofuran was added a solution of tetrabutylammonium fluoride (1.0M, in tetrahydrofuran, 1.32 ml) under an atmosphere of nitrogen. After 18 hours, the mixture was diluted with water (20 ml) and extracted with ethyl ether (4×30 ml). The combined ether extracts were washed with brine, dried (anhydrous MgSO$_4$), filtered and evaporated in vacuo to give an oil. This was chromatographed on a column of silica gel (80 g, Baker 60-200 mesh) eluting with ethyl ether-hexane (1:4) to give 285 mg (87.9%) of the tlc-homogeneous analytical specimen of title compound, $[\alpha]^{25}_D (-)20°$ (c=0.57, CHCl$_3$) as an oil with consistent mass, IR (3338 cm$^{-1}$, OH, strong; 1650 cm$^{-1}$, C=N medium), H$^1$-NMR and C$^{13}$-NMR spectral data.

Anal calcd for C$_{29}$H$_{44}$FNO$_4$: C, 71.13; H, 9.06; F, 3.88; N, 2.86; Found: C, 71.09; H, 9.15; F, 3.79; N, 2.84

EXAMPLE 16

(1α,2β,3β,4α)-7-[3-[(Hexyloxy)methyl]-7-oxabicyclo[2.2.1]hept-2-yl]-N-hydroxy-2,2-dimethyl heptanimidic acid, phenylmethyl ester

A.

(1α,2β,3β,4α)-7-[3-[(Hexyloxy)methyl]-7-oxabicyclo[2.2.1]hept-2-yl]-2,2-dimethylheptanoic acid Example 1 Part L acid compound (198 mg, 0.54 mmol) is dissolved in 10 ml of methanol and is hydrogenated in the presence of 5% Pd/C (25 mg) until no double bond is visible in the $^1$H NMR spectrum.

B.

(1α,2β,3β,4α)-7-[3-[(Hexyloxy)methyl]-7-oxabicyclo[2.2.1]hept-2-yl]-N-hydroxy-2,2-dimethylheptanimidic acid, phenylmethyl ester Following the procedure of Example 1 from Part M except substituting the above Part A acid for Example 1 Part L acid, the title compound is obtained.

EXAMPLE 17

[1R-[1α,2β(5Z),3β,4α]]-7-[3-[(Hexylthio)methyl]-7-oxabicyclo[2.2.1]hept-2-yl]-N-hydroxy-2,2-dimethyl-5-heptenimidic acid, phenylmethyl ester

A.

[1R-[1α,2β(5Z),3β,4α]]-7-[3-(Hydroxymethyl)-7-oxabicyclo[2.2.1]hept-2-yl]-5-heptenoic acid, methyl ester The above title A compound was prepared as described in Example 1, Part F.

B.

[1R-[1α,2β-(5Z),3β,4α]]-7-[3-[(Hexylthio)methyl]-7-oxabicyclo[2.2.1]hept-2-yl]-5-heptenoic acid, methyl ester A solution of 274 mg (1.02 mmol) of Part A alcohol in 2 ml of dry pyridine is cooled to 0° C. To this stirred solution is added 295 mg (1.53 mmol) of tosyl chloride. After 4 hours, the reaction mixture is diluted with 15 ml each of ether and saturated NaHCO$_3$ solution. The aqueous layer is extracted with 25 ml of ether. The combined ether layers are washed twice with 30 ml of 1N HCl, dried over MgSO$_4$, filtered, and concentrated in vacuo. The crude product is chromatographed on 32 g of silica gel using 4:1 hexane-ether as eluant. This gives pure tosylate along with a mixture of tosylate and its 5,6-double trans bond isomer.

To a solution of 105 mg (0.93 mmol) of potassium t-butoxide in 10 ml of THF is added 0.45 ml (3.1 mmol) of 1-hexanethiol. To this stirred slurry is added a solution of 270 mg (0.64 mmol) of the above tosylate in 5 ml THF. The reaction mixture is heated to reflux for 5 hours. The cooled reaction mixture is partitioned between 30 ml each of saturated NaHCO$_3$ solution and ether. The aqueous layer is extracted with 2×30 ml of ether. The combined organic extracts are dried over MgSO$_4$, filtered and concentrated in vacuo. The crude product is chromatographed on 30 g of silica gel using 4:1 hexane-ether as eluant to afford title B thioether.

C.

[1R-[1α,2β(5Z),3β,4α]]-7-[3-[(Hexylthio)methyl]-7-oxabicyclo[2.2.1]hept-2-yl]-5-heptenoic acid A solution of 222 mg (0.60 mmol) of Part B thioether in 15 ml of THF and 1.9 ml H$_2$O is purged with a stream of argon for 10 minutes. To this stirred solution is added 2.4 ml of argon-purged 1N LiOH solution. This mixture is stirred vigorously for 7 hours at room temperature. The reaction mixture is partitioned between 25 ml each of brine and EtOAc. The aqueous layer is acidified to pH=2.5 by the addition of 1N HCl and then shaken with the original EtOAc layer. The aqueous layer is extracted with 2×25 ml EtOAc. The combined EtOAC layers are dried over MgSO$_4$, filtered and concentrated in vacuo. Purification is effected by flash chromatography on 30 g of silica gel using 2:1 hexane-ether as eluant to afford title acid.

D.

[1R-[1α,2β(5Z),3β,4α][-7-[3-[(Hexylthio)methyl]-7-oxabicyclo[2.2.1]hept-2-yl]-N-hydroxy-2,2,-dimethyl-5-heptenimidic acid, phenylmethyl ester Following the procedure of Example 1 except substituting the above Part C acid for the Example 1 Part I acid, the title compound is obtained.

EXAMPLE 18

[1α,2β(5Z),3β,4α]-7-[3-[(Methoxy)methyl]-7-oxabicyclo[2.2.1]hept-2-yl]-1-methoxy-2,2-dimethyl-5-heptenylidene]hydroxylamine Following the procedure of Example 2 except substituting methyl methanesulfonate for n-hexyl methanesulfonate, the title compound is obtained.

EXAMPLE 19

(1α,2β,3β,4α)-7-[3-[(Butyloxy)methyl]-7-oxabicyclo[2.2.1]hept-2-yl]-N-hydroxy heptanimidic acid, hexyl ester Following the procedure of Examples 5 and 16 except substituting n-butyl methanesulfonate for n-hexyl methanesulfonate in Example 1 Part G and not doing parts J and K, the title compound is obtained.

EXAMPLE 20

[1α,2β(5Z),3β,4α]-7-[3-[(Octyloxy)methyl]-7-oxabicyclo[2.2.1]hept-2-yl]-N-hydroxy-5-heptenimidic acid, phenylmethyl ester Following the procedure of Example 1 Part G (without doing Parts J and K) except substituting n-octyl methanesulfonate for n-hexyl methanesulfonate, the title compound is obtained.

EXAMPLE 21

[1α,2β(5Z),3β,4α]-7-[3-(Phenoxy)methyl]-7-oxabicyclo[2.2.1]hept-2-yl]-N-hydroxy-5-heptenimidic acid, phenylmethyl ester (a) Phenol (1 mmol) is added to a solution of triphenylphosphine (1 mmol), diethylazodicarboxylate (1 mmol) and title F alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(Z),3β,4α]-7-[3-[(phenyloxy)methyl]-7-oxabicyclo[2.2.1]hept-2-yl]-5-heptenoic acid, methyl ester.

(b) Following the procedure as set out in Example 1 Parts K to P, the ester from part (a) is converted to the title compound.

EXAMPLE 22

[1α,2β(5Z),3β,4α]-7-[3-[(Ethoxy)methyl]-7-oxabicyclo[2.2.1]hept-2-yl]-N-hydroxy-2,2-dimethyl-5-heptenimidic acid, 1-methylethyl ester Following the procedure of Examples 1 through Part N and Example 4 except substituting ethyl methanesulfonate for n-hexylmethane sulfonate in Example 1 Part G, the title compound is obtained.

EXAMPLE 23

[1α,2β(5Z),3β,4α]-7-[3-[(Phenoxy)methyl]-7-oxabicyclo[2.2.1]hept-2-yl]-N-hydroxy-2,2-dimethylheptnimidic acid, phenylmethyl ester Following the procedure of Examples 21 and 1 except substituting the Example 21 Part A compound for the Example 1 Part L acid compound, the title compound is obtained.

EXAMPLE 24

[1α,2β(5Z),3β,4α]-7-[3-[(Benzyloxy)methyl]-7-oxabicyclo[2.2.1]hept-2-yl]-N-hydroxy-2,2-dimethyl-5-heptenimidic acid, dodecyl ester Following the procedure of Example 1 up through Part N and Example 6 except substituting benzyl methanesulfonate for n-hexylmethane sulfonate in Example 1 Part G, the title compound is obtained.

EXAMPLE 25

(1α,2β,3β,4α)-7-[3-[(Benzyloxy)methyl]-7-oxabicyclo[2.2.1]hept-2-yl]-N-hydroxy-2,2-dimethylheptanimidic acid, phenylmethyl ester Following the procedure of Example 16 Part A except substituting the Example 1 Part G compound for the Example 1 Part L acid and then following the procedure of Example 1 Part G except substituting benzyl tosylate for n-hexyl mesylate, the title compound is obtained.

EXAMPLE 26

[1α,2β(5Z),3β,4α]-5-[3-[(Cyclohexyloxy)methyl]-7-oxabicyclo[2.2.1]hept-2-yl]-N-hydroxy-3-pentenimidic acid, phenylmethyl ester Following the procedure of Example 7 except substituting cyclohexyl methanesulfonate for n-hexyl methanesulfonate in Part D, the title compound is obtained.

EXAMPLE 27

[1α,2β(5Z),3β,4α]-7-[3-[(Cyclopentyloxy)methyl]-7-oxabicyclo[2.2.1]hept-2-yl]-N-hydroxy-2,2-dimethyl-5-heptenimidic acid, phenylmethyl ester Following the procedure of Example 1 except substituting cyclopentyl methanesulfonate for n-hexyl methanesulfonate in Part G, the title compound is obtained.

EXAMPLE 28

(1α,2β,3β,4α)-7-[3-[(Cyclohexyloxy)methyl]-7-oxabicyclo[2.2.1]hept-2-yl]-N-hydroxy-2,2-dimethylheptanimidic acid, phenylmethyl ester Following the procedure of Example 16 except substituting the acid prepared in Example 16 Part A for the Example 1 Part L acid, the title compound is obtained.

EXAMPLE 29

[1α,2β(5Z),3β,4α]-7-[3-[2-(Hexyloxy)ethyl]-7-oxabicyclo[2.2.1]hept-2-yl]-N-hydroxy-2,2-dimethyl-5-heptenimidic acid, phenylmethyl ester

A.

[1α,2β(5Z),3β,4α]-7-[[3-(2-Oxo)ethyl]-7-oxabicyclo[2.2.1]hept-2-yl]-5-heptenoic acid, methyl ester Into a dry 100 ml round bottom 3-necked flask containing a stir bar is added dried methoxymethyltriphenylphosphonium chloride (($C_6H_5$)$_3P^+$—CH$_2$OCH$_3$Cl$^-$) (12.9 g, 37.7 mmol) and 235 ml distilled toluene (stored over molecular sieves). The resulting suspension is stirred in an ice-bath, under argon, until cold and then a 1.55M solution of 18.3 ml (28.3 mmol) of potassium t-amylate in toluene was added dropwise. A bright red solution formed which is stirred at 0° C. for an additional 35 minutes. Thereafter, a solution of 4.8 g (18.8 mmol) of [1β,2α(5Z),3α,4β]-7-(3-formyl)-7-oxabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) of acetic acid in 5 ml ether. The mixture is immediately poured into 200 ml saturated NH$_4$Cl, and extracted with ether (4×200 ml). The combined ether phases are washed with NaCl saturated solution, and dried (MgSO$_4$ anhydrous) and concentrated to yield a yellow oil in a white crystalline solid (triphenylphosphine oxide). This is washed with EtOAc and the material in the washings is purified by chromatography on an LPS-1 silica gel column. The fractions obtained are (A) [1α,2β(5Z), 3β,4α]-7-[[3-(2-oxo)ethyl]-7-oxabicyclo[2.2.1]hept-2-yl]-5-heptenoic acid, methyl ester, (B) [1α,2β(5Z),3β,4α]-7-[3-(2-methoxy)ethendiyl]-7-oxabicyclo[2.2.1]hept-2-yl]-5-heptenoic acid, methyl ester, and (C) [1α,2β(5Z),3β,4α]-7-[[3-(2,2-dimethoxy)ethyl]-7-oxabicylo[2.2.1]hept-2-yl]-5-heptenoic acid, methyl ester.

Compounds (B) and (C) are each treated with trifluoroacetic acid to convert each to compound (A).

B.

[1α,2β(5Z),3β,4α]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$anhydrous). The ether is evaporated to yield the title B compound.

C.

[1α,2β(5Z),3β,4α]-7-[3-(2-(Hexyloxy)ethyl]-7-oxabicyclo[2.2.1]hept-2-yl]-2,2-dimethyl-5-heptenoic acid Following the procedure of Example 1 Parts G to L except substituting the above part B alcohol for the alcohol used in Example 1 Part G, the title compound is obtained.

D.

[1α,2β(5Z),3β,4α]-7-[3-[2-(Hexyloxy)ethyl]-7-oxabicyclo[2.2.1]hept-2-yl]-N-hydroxy-2,2-dimethyl-5-heptenimidic acid, phenylmethyl ester Following the procedure of Example 1 Part M to P except substituting the above Part C acid for the Example 1 Part L acid, the title compound is obtained.

EXAMPLE 30

[1α,2β(5Z),3β,4α]-7-[3-[2-(Benzyloxy)ethyl]-7-oxabicyclo[2.2.1]hept-2-yl]-N-hydroxy-2,2-dimethyl-5-heptenimidic acid, phenylmethyl ester Following the procedure of Example 29 except substituting benzyl methanesulfonate for n-hexyl methanesulfonate, the title compound is obtained.

EXAMPLE 31

[1α,2β(5Z),3β,4α]-7-[3-[2-(Cyclopentyloxy)ethyl]-7-oxabicyclo[2.2.1]hept-2-yl]-N-hydroxy-2,2-dimethyl-5-heptenimidic acid, phenylmethyl ester Following the procedure of Example 29 except substituting cyclopentyl methanesulfonate for n-hexyl methanesulfonate, the title compound is obtained.

EXAMPLE 32

[1α,2β(5Z),3β,4α]-7-[3-[2-(Cyclohexyloxy)ethyl]-7-oxabicyclo[2.2.1]hept-2-yl]-N-hydroxy-2,2-dimethyl-5-heptenimidic acid, hexyl ester Following the procedure of Examples 26 and 5 except substituting cyclohexyl methanesulfonate for n-hexyl methanesulfonate, the title compound is obtained.

EXAMPLE 33

[1α,2β(5Z),3β,4α]-7-[3-[4-(Hexyloxy)butyl]-7-oxabicyclo[2.2.1]hept-2-yl]-N-hydroxy-2,2-dimethyl-5-heptenimidic acid, phenylmethyl ester

A.

[1α,2β(5Z),3β,4α]-7-[[3-(3-Oxo)propyl]-7-oxabicyclo[2.2.1]hept-2-yl]-5-heptenoic acid, methyl ester Following the procedure of Example 29, Part A except substituting [1α,2β(5Z),3β,4α]-7-[[3-(2-oxo)ethyl]-7-oxabicyclo[2.2.1]hept-2-yl]-5-heptenoic acid, methyl ester for [1β,2α(5Z),3α,4β]-7-[[3-formyl]-7-oxabicyclo[2.2.1]hept-2-yl]-5-heptenoic acid, methyl ester, the title A compound is obtained.

B.

[1α,2β(5Z),3β,4α]-7-[3-(4-Oxo)butyl-7-oxabicyclo[2.2.1]hept-2-yl]-5-heptenoic acid, methyl ester Following the procedure of Example 29, part A, except substituting the aldehyde from part A above for [1α,2β(5Z),3β,4α]-7-[[3-formyl]-7-oxabicyclo[2.2.1-]hept-2-yl]-5-heptenoic acid, methyl ester, the title B compound is obtained.

C.

[1α,2β(5Z),3β,4α]-7-[3-(4-Hydroxybutyl)-7-oxabicyclo[2.2.1]hept-2-yl]-5-heptenoic acid, methyl ester Following the procedure of Example 29, part B, except substituting the title B aldehyde for [1α,2β(5Z),3β,4α]-7-[[3-(2-oxoethyl)-7-oxabicyclo[2.2.1]hept-2-yl]-5-heptenoic acid, methyl ester, the title C alcohol is obtained.

D.

[1α,2β(5Z),3β,4α]-7-[3-[4-(Hexyloxy)butyl]-7-oxabicyclo[2.2.1]hept-2-yl]-5-heptenoic acid Following the procedure of Example 1, except substituting the above part C alcohol for the alcohol used in Example 1 part G, the title compound is obtained.

E.

[1α,2β(5Z),3β,4α]-7-[3-[4-(Hexyloxy)butyl]-7-oxabicyclo[2.2.1]hept-2-yl]-N-hydroxy-2,2-dimethyl-5-heptenimidic acid, phenylmethyl ester Following the procedure of Example 1M to 1P except substituting the above Part D acid for Example 1 Part I acid, the title compound is obtained.

EXAMPLE 34

[1α,2β(5Z),3β,4α]-7-[3-[4-(Cyclohexyloxy)butyl]-7-oxabicylco[2.2.1.]hept-2-yl]-2,2-dimethyl-N-(phenylmethoxy)-5-heptenimidic acid, 2-phenylethyl ester Following the procedure of Example 33 to Part D and Example 9 except substituting cyclohexyl methanesulfonate for n-hexyl methanesulfonate, the title compound is obtained.

EXAMPLE 35

[1α,2β(5Z),3β,4α]-7-[3-[(Propylthio)methyl]-7-oxabicyclo[2.2.1]hept-2-yl]-2,2-dimethyl-N-(phenylmethoxy)-5-heptenimidic acid, phenylmethyl ester Following the procedure of Example 17, Example 1 through Part M and Example 10 except substituting propylmercaptan for 1-hexanethiol, the title compound is obtained.

EXAMPLE 36

(1α,2β,3β,4α)-7-[3-[(Cyclohexylthio)methyl]-7-oxabicyclo[2.2.1]hept-2-yl]-N-hydroxy-2,2-dimethyl-heptanimidic acid, phenylmethyl ester Following the procedure of Examples 16 and 17 except substituting cyclohexylmercaptan for 1-hexanethiol, the title product is obtained.

EXAMPLE 37

[1α,2β(5Z),3β,4α]-7-[3-[2-(Hexylthio)ethyl]-7-oxabicyclo[2.2.1]hept-2-yl]-N-hydroxy-2,2-dimethyl-5-heptenimidic acid, phenylmethyl ester Following the procedure of Examples 29 and 16 except substituting the Example 29 part B alcohol for the alcohol used in Example 16, the title compound is obtained.

EXAMPLES 38 AND 39

[1α,2β(5Z),3β,4α]-7-[3-[(Hexylsulfinyl)methyl]-7-oxabicyclo[2.2.1]hept-2-yl]-N-hydroxy-2,2-dimethyl-5-heptenimidic acid, phenylmethyl ester (Example 38)

and

6[1α,2β(5Z),3β,4α]-7-[3-[(Hexylsulfonyl)methyl]-7-oxabicyclo[2.2.1]hept-2-yl]-N-hydroxy-2,2-dimethyl-5-heptenimidic acid, phenylmethyl ester (Example 39)

To a solution of 634 mg (1.72 mmol) of [1α,2β(5Z),3β,4α]-7-[3-([hexylthio)methyl]-7-oxabicyclo[2.2.1]hept-2-yl]-2,2-dimethyl-5-heptenimidic acid, phenylmethyl ester (prepared as described in Example 17) in 6.78 ml of methanol at 0° C. is added dropwise over 4 minutes 4.8 ml of 0.5M aqueous sodium periodate solution. Tetrahydrofuran (2 ml) is then added and the resulting reaction mixture is stirred at room temperature for 15 hours. A precipitate is removed by filtration and washed with ether (3×50 ml). The filtrate is washed with 60 ml of saturated aqueous NaHCO3 solution and dried over anhydrous magnesium sulfate. Concentration in vacuo affords an oily crude product. This is chromatographed on silica gel 60 using 0.5–1.0% CH3OH in CH2Cl2 as eluant. This gives [1α,2β(5Z),3β,-4α]-7-[3-[(hexylsulfinyl)methyl]-7-oxabicyclo[2.2.1-]hept-2-yl]-2,2-dimethyl-5-heptenimidic acid, phenylmethyl ester and [1α,2β(5Z),3β,4α]-7-[3-[(hexylsulfonyl)methyl]-7-oxabicyclo[2.2.1]hept-2-yl]-2,2-dimethyl-5-heptenimidic acid, phenylmethyl ester.

EXAMPLE 40

[1α,2β(5Z),3β,4α]-N-[7-[3-[(Ethylsulfinyl)methyl]-7-oxabicyclo[2.2.1]hept-2-yl]-1-methoxy-2,2-dimethyl-5-heptenylidene]hydroxylamine Following the procedure of Examples 2, 17 and 38, title compound is obtained.

EXAMPLE 41

(1α,2β,3β,4α)-N-[7-[3-[(Heptylsulfinyl)methyl]-7-oxabicyclo[2.2.1]hept-2-yl]-2,2-dimethyl-1-propoxyheptanylidene]hydroxylamine Following the procedure of Examples 3, 17, and 38 except substituting 1-heptanethiol for 1-hexanethiol, the title compound is obtained.

EXAMPLE 42

[1α,2β(5Z),3β,4α]-7-[3-[(Octylsulfonyl)methyl]-7-oxabicyclo[2.2.1]hept-2-yl]-N-hydroxy-2,2-dimethyl-5-heptenimidic acid, phenylmethyl ester Following the procedure of Examples 1, 17 and 39 except substituting octylmercaptan for 1-hexanethiol, the title compound is obtained.

EXAMPLE 43

[1α,2β(5Z),3β,4α]-7-[3-[(Propylsulfonyl)methyl]-7-oxabicyclo[2.2.1]hept-2-yl]-N-hydroxy-2,2-dimethyl-5-heptenimidic acid, 2-propenyl ester Following the procedure of Examples 1 and 12 and 39 except substituting propylmercaptan for 1-hexanethiol, the title compound is obtained.

EXAMPLE 44

[1α,2β(5Z),3β(E),4α]-7-[3-[[(3-Cyclohexyl-2-propenyl)oxy]methyl]-7-oxabicyclo[2.2.1]hept-2-yl]-N-hydroxy-2,2-dimethyl-5-heptenimidic acid, phenylmethyl ester Following the procedure of Example 1 except substituting (E)-3-cyclohexyl-2-propenylmesylate for 1-hexyl mesylate, the title compound is obtained.

EXAMPLE 45

[1α,2β(5Z),3β,4α]-7-[3-[[(3-Ethyl-3-octenyl)thio]methyl]-7-oxabicyclo[2.2.1]hept-2-yl]-N-hydroxy-2,2-dimethyl-5-heptenimidic acid, phenylmethyl ester Following the procedure of Example 17 except substituting 3-ethyl-3-octenylthiol for 1-hexanethiol, the title compound is obtained.

EXAMPLE 46

[1α,2β(5Z),3β,4α]-7-[3-[[(8-Phenyl-5-octynyl)thio]methyl]-7-oxabicyclo[2.2.1]hept-2-yl]-N-hydroxy-2,2-dimethyl-5-heptenimidic acid, phenylmethyl ester Following the procedure of Example 17 except substituting 8-phenyl-5-octynylthiol for 1-hexanethiol, the title compound is obtained.

EXAMPLE 47

[1α,2β(5Z),3β,4α]-7-[3-[[(9-Cyclohexyl-3-nonynyl)oxy]methyl]-7-oxabicyclo[2.2.1]hept-2-yl]-N-hydroxy-2,2-dimethyl-5-heptenimidic acid, phenylmethyl ester Following the procedure of Example 1 except substituting 9-cyclohexyl-3-nonynylmesylate for 1-hexylmesylate, the title compound is obtained.

EXAMPLE 48

[1R-[1α,2β(3Z),3β,4α]-5-[3-[(Hexyloxy)methyl]-7-oxabicyclo[2.2.1]hept-2-yl]-pent-3-enoic acid

A. 3-Bromo-1-tetrahydropyranyloxy propane

A solution of 3-bromo-1-propanol (10 mmole) in dichloromethane (20 ml) containing pyridinium p-toluene sulfonate (150 mg) is stirred with dihydropyran (15 mmole) for 20 hours at ambient temperature. The solution is then washed with water, dried (MgSO$_4$ anhydrous), evaporated and is chromatographed on silica gel to afford the title compound.

B. 1-Tetrahydropyranyloxypropyl-3-(triphenyl)phosphonium bromide

A solution of Part A compound (5 mmol) is refluxed with triphenylphosphine (5 mmol) under nitrogen in acetonitrile (30 ml) for 20 hours. The mixture is then concentrated and is diluted with dry ether to precipitate the title compound as a colorless solid. This is dried in vacuo prior to use.

C.
[1R-[1α,2β(3Z),3β,4α]-5-[3-[(Hydroxy)methyl]-1-tetrahydropyranyloxy-7-oxabicyclo[2.2.1]hept-2-yl]-pent-3-enol To a stirred mixture of Part B phosphonium salt (5.5 mmole) and Example 1, Part E hemiacetal (5 mmol) in dry tetrahydrofuran (25 ml) in an ice bath is added a 1M solution of K-t-amylate in toluene (6 mmole). The mixture is then stirred at room temperature for 20 hours and is made acidic by the addition of a few drops of acetic acid. It is then concentrated in vacuo, diluted with water and extracted with ethyl acetate. The extracts are combined, washed with water, dried (MgSO$_4$ anhydrous), evaporated and the residue is chromatographed on silica gel to isolate the title compound.

D.
[1R-[1α,2β(3Z),3β,4α]-5-[3-[(Hexyloxy)methyl]-1-tetrahydropyranyloxy-7-oxabicyclo[2.2.1]hept-2-yl]-pent-3-enol Part C compound (5 mmol) is reacted with n-hexylmesylate as described in Example 1, Part G to afford the title compound.

E.
[1R-[1α,2β(3Z),3β,4α]-5-[3-[(Hexyloxy)methyl]-7-oxabicyclo[2.2.1]hept-2-yl]-pent-3-enol A solution of Part D compound (5 mmole) in methanol (25 ml) containing pyridinium p-toluene sulfonate (150 mg) is refluxed for 4 hours. The solution is then concentrated in vacuo, diluted with water and extracted with ethyl acetate. The extracts are combined, washed with a dilute sodium bicarbonate solution and water, dried (MgSO$_4$ anhydrous) and is evaporated to an oil. This is chromatographed on silica gel to afford the title compound.

F.
[1R-[1α,2β(3Z),3β,4α]-5-[3-[(Hexyloxy)methyl]-7-oxabicyclo[2.2.1]hept-2-yl]-pent-3-enoic acid A solution of Part F alcohol (5 mmol) in acetone (30 ml) is stirred in an ice bath and a modest excess of Jones' reagent is added dropwise. After 1 hour, the mixture is diluted with water (150 ml) and is extracted with ethyl acetate. The extracts are combined, washed several times with small amounts of water, dried (MgSO4 anhydrous) and is evaporated to afford the crude product as an oil. This is chromatographed on silica gel to isolate the title compound.

The title acid may be employed in place of the Example 1 Part I or Part L acid to form compounds of the invention.

EXAMPLE 49

[1R-[1α,2β(2E),3β,4α]-4-[3-(Hexyloxy)methyl]-7-oxabicyclo[2.2.1]hept-2-yl]-but-2-enoic acid

A.
[1R-[1α,2β(2E),3β,4α]-4-[3-(Hydroxy)methyl]-7-oxabicyclo[2.2.1]hept-2-yl]-but-2-enoic acid, methyl ester A solution of trimethyl phosphono acetate (5 mmol) in dry tetrahydrofuran (20 ml) is stirred in an ice bath for 1 hour with 50% sodium hydride/paraffin (5 mmole). A solution of Example 1, Part E hemiacetal is then added and the mixture is stirred in the ice bath for 20 hours. It is then concentrated in vacuo and diluted with water. The product is isolated by extraction with ethyl acetate and is purified by chromatography to afford the title compound.

B.
[1R-[1α,2β(2E),3β,4α]-4-[3-(Hexyloxy)methyl]-7-oxabicyclo[2.2.1]hept-2-yl]-but-2-enoic acid Part A ester (5 mmole) and n-hexylmesylate are reacted as described in Example 1, Part G and the crude product is hydrolyzed with lithium hydroxide as described in Example 1, Part L to afford the title compound after chromatography on silica gel.

The title compound may be employed in place of Example 1 Part I or Part L acid to form compounds of the invention.

EXAMPLE 49A

[1R-[1α,2β(Z),3β,4α]]-7-[3-[(Hexyloxy)methyl]-7-oxabicyclo[2.2.1]hept-2-yl]-N-hydroxy-2,2-dimethyl-5-heptenimidic acid, 2-propenyl ester

A.
[1R-[1α,2β(Z),3β,4α]]-7-[3-[(Hexyloxy)methyl]-7-oxabicyclo[2.2.1]hept-2-yl]-N-[[(dimethyl)(1,1-dimethylethyl)silyl]oxy]-2,2-dimethyl-5-heptenimidic acid, 2-propenyl ester To a chilled (0°, ice bath) and stirred solution of 50% sodium hydride in paraffin (53 mg, 1.1 mmole) in 2.5 ml of dry dimethylformamide under an atmosphere of nitrogen was added a solution of Example 1 Part N compound (496 mg, 1.0 mmole) in 2.5 ml of dry dimethylformamide. After 1.5 hours at 0°, allyl bromide (0.35 ml, 4 mmole, filtered through a short column of basic alumina) was added dropwise and the solution was gradually warmed to room temperature. After 18 hours, the mixture was diluted with water (20 ml) and extracted with ethyl ether (4×30 ml). The combined ether extracts were washed with brine, dried over anhydrous MgSO4 and evaporated in vacuo to give an oil. A tlc examination (silica gel, EtOAc-hexane 1:4) showed one major less polar spot and four other minor components. This was chromatographed on a column of silica gel (150 g, Baker 60–200 mesh) eluting with ethyl ether-hexane (5:95) to give 368 mg (68.7%) of title compound with consistent H¹-NMR and C¹³-NMR spectra.

B.
[1R-[1α,2β(Z),3β,4α]]-7-[3-[(Hexyloxy)methyl]-7-oxabicyclo[2.2.1]hept-2-yl]-N-hydroxy-2,2-dimethyl-5-heptenimidic acid, 2-propenyl ester To a stirred solution of Part A compound (368 mg, 0.687 mmole), in dry tetrahydrofuran was added a solution of tetrabutylammonium fluoride (1.0M in tetrahydrofuran, 1.4 ml, 1.4 mmole) under an atmosphere of nitrogen. After 18 hours, the mixture was diluted with water (20 ml) and extracted with ethyl ether (4×30 ml). The combined ether extracts were washed with brine, dried over anhydrous MgSO4, filtered and evaporated in vacuo to give an oil. This was chromatographed on a column of silica gel (100 g, Baker 60–200 mesh) eluting with ethyl ether-hexane (1:4) to give 265 mg (91.5%) of the tlc-homogeneous analytical specimen of title compound $[\alpha]_D = -20.3°$ (c=0.69, CHCl3) with consistent mass, IR (3345 cm⁻¹, OH, strong; 1647 cm⁻¹, C=N, medium), H¹-NMR and C¹³-NMR spectral data.

Anal Calcd for C25H43NO4: C, 71.22; H, 10.28; N, 3.32; Found: C, 71.40; H, 10.42; N, 3.49

EXAMPLE 50

[1R-[1α,2β,3β,4α]]-7-[3-[(Hexyloxy)methyl]-7-oxabicyclo[2.2.1]hept-2-yl]N-methoxy-2,2-dimethyl-5-heptenimidic acid, phenylmethyl ester To a chilled (0°, ice bath) and stirred suspension of 50% sodium hydride-paraffin (32 mg, 0.66 mole) in 1.0 ml of dry dimethylformamide under an atmosphere of nitrogen was added a solution of Example 1 Part P ester in 0.5 ml of dry dimethylformamide. After 1 hour at 0°, methyl iodide (0.132 ml, 2.12 mmole) was added dropwise and the mixture was gradually warmed to room temperature. After 18 hours, the resulting solution was diluted with water (25 ml) and extracted with ethyl ether (4×30 ml). The combined ether extracts were washed with brine, dried (anhydrous MgSO4), filtered and evaporated in vacuo to give an oil. This was chromatographed on a column of silica gel (70 g, Baker 60–200 mesh) eluting with ethyl ether-hexane (1:9) to give 250 mg (97.1%) of the tlc-homogeneous analytical specimen of title compound as an oil $[\alpha]_D^{25} = (+)1.7°$ (c=0.97, CHCl3) with consistent mass, IR (1626 cm⁻¹, C=N, medium), H¹-NMR and C¹³-NMR spectral data.

Anal calcd for C30H47H47NO4: C, 74.18; H, 9.76; N, 2.88; Found: C, 74.33; H, 9.85; N, 2.83

EXAMPLE 50A

[1R-[1α,2β(5Z),3β,4α]]-7-[3-[(Hexyloxy)methyl]-7-oxabicyclo[2.2.1]hept-2-yl]-N-acetyloxy-2,2-dimethyl-5-heptenimidic acid, phenylmethyl ester A solution of [1R-[1α,2β(5Z),3β,4α]]-7-[3-[(hexyloxy)methyl]-7-oxabicyclo[2.2.1]hept-2-yl]-N-hydroxy-2,2-dimethyl-5-heptenimidic acid, phenylmethyl ester (Example 1, part P), (200 mg) in dry pyridine (3.0 ml) is allowed to stand at room temperature for 20 hours. The mixture is then concentrated in vacuo, diluted with ether, washed with ice-cold 0.5N hydrochloric acid, a dilute NaHCO3 solution and water, dried (MgSO4 anhydrous) and is evaporated to afford the title product as an oil. This is chromatographed on a column of silica gel to isolate the homogeneous title product.

EXAMPLE 50B

[1R-[1α,2β(5Z),3β,4α]]-7-[3-[(Hexyloxy)methyl]-7-oxabicyclo[2.2.1]hept-2-yl]-N-benzoyloxy-2,2-dimethyl-5-heptenimidic acid, phenylmethyl ester By following the procedure of Example 50A but using benzoyl chloride instead of acetic anhydride and carrying out the reaction at reduced temperature (0° to −20°), the title product is prepared.

EXAMPLES 51 AND 51A TO 61

It will also be appreciated that compounds of the invention wherein $R^1$ is alkanoyl or aroyl may be prepared by treating the compound of Table I, Column IV, with

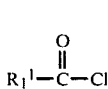

(wherein $R_1^1$ is alkyl or aryl) in the presence of pyridine.

TABLE I

| Ex. No. | Column I<br>$Br^-(C_6H_5)_3P^+(CH_2)_{\overline{m}}COOH$<br>m | Column II<br>$R^2Br/R^2OMes$<br>$R^2$ | Column III<br>RBr/ROMes<br>R | Column IV $\begin{array}{c}\phantom{x}\\ CH_2-CH=CH+CH_2)_{\overline{m}}C=N-OH\\ CH_2-O-R^2\end{array}$ OR | | |
|---|---|---|---|---|---|---|
| | | | | m | $R^2$ | R |
| 51. | 3 | $C_2H_5$ | $C_2H_5$ | | | |
| 51A. | 4 | $C_6H_5$ | $CH_2C_6H_5$ | as in Column I | as in Column II | as in Column III |
| 52. | 4 | $-CH_2C_6H_5$ | $C_3H_7$ | | | |
| 53. | 1 | ⬡ | $-CH_2C_6H_5$ | | | |
| 54. | 4 | $-CH_2-$⬡ | $-CH=CH_2$ | | | |
| 55. | 5 | $-CH_2-CH=CH-CH_3$ | $C_2H_5$ | | | |
| 56. | 6 | $-CH_2C{\equiv}CCH_2CH_3$ | $C_5H_{11}$ | | | |
| 57. | 4 | $-CH(CH_3)-$⬡ | $CH_2CH_2C_6H_5$ | | | |
| 58. | 5 | ⬡-OH | $C_4H_9$ | | | |
| 59. | 6 | $C_8H_{17}$ | $-(CH_2)_2-C_6H_5$ | | | |
| 60. | 7 | $-(CH_2)_2C_6H_5$ | $C_3H_7$ | | | |
| 61. | 8 | △ | $-CH_2-CH=CH_2$ | | | |

Following the procedure of Example 1 except replacing the 4-carboxybutyl triphenylphosphonium bromide with the compound shown in Column I, replacing n-hexylmesylate in Example 1 Part G with the compound shown in Column II of Table I set out below and replacing benzyl bromide in Example 1 Part O with the compound shown in Column III, the product shown in Column IV is obtained (wherein A is —CH=CH—).

EXAMPLES 62 TO 73

Following the procedure of Example 17 and Example 1 except replacing the 4-carboxybutyltriphenylphosphonium bromide with the compound shown in Column I, replacing tosyl chloride in Example 17 Part B with the compound shown in Column II of Table II set out below and replacing benzyl bromide (in Example 1 Part O) with the compound shown in Column III, the product shown in Column IV is obtained.

TABLE II

| Ex. No. | m | $R^2$ | R |
|---|---|---|---|
| | Column I<br>$Br^-(C_6H_5)_3P^+-(CH_2)_m-COOH$ | Column II<br>$R^2SH$ | Column III<br>R—Br/ROMe |
| 62. | 3 | $C_2H_5$ | $C_7H_{15}$ |
| 63. | 4 | $C_6H_5$ | $CH_2CH_2C_6H_5$ |
| 64. | 4 | $-CH_2C_6H_5$ | $C_3H_7$ |
| 65. | 6 | ⬡ | $-CH_2C_6H_5$ |

TABLE II-continued

| Ex. No. | m | R² | R |
|---|---|---|---|
| 66. | 5 | —CH₂—(cyclohexyl) | —CH₂—CH=CH₂ |
| 67. | 4 | —CH₂—CH=CH—CH₃ | C₂H₅ |
| 68. | 3 | —CH₂C≡CCH₂CH₃ | 2-pyridyl-CH₂— |
| 69. | 4 | —CH(CH₃)—C₆H₅ | CH₂C₆H₅ |
| 70. | 5 | —C₆H₄—OH | C₄H₉ |
| 71. | 6 | C₈H₁₇ | —(CH₂)₂—C₆H₅ |
| 72. | 7 | —(CH₂)₂C₆H₅ | 3-pyridyl-(CH₂)₂— |
| 73. | 8 | cyclopentyl | —CH₂—CH=CH₂ |

Column IV norbornyl-CH₂—CH=CH—(CH₂)ₘ—C(OR)=N—OH with CH₂—S—R²

| as in Column I | as in Column II | as in Column III |

EXAMPLES 74 TO 85

Following the procedure of Examples 1 and 9 and optionally Example 16 except replacing the 4-carboxybutyl triphenylphosphonium bromide with the compound shown in Column I, replacing n-hexylmesylate in Example 1 Part G with the compound shown in Column II of Table III set out below and in Example 9, replacing O-benzylhydroxylamine hydrochloride with the compound shown in Column III (R¹ONH₂•HCl) and replacing phenethyl alcohol with the compound shown in Column IV (ROH), the product shown in Column V is obtained wherein A is —CH=CH— where Example 16 is not followed, and A is (CH₂)₂ where Example 16 is followed.

TABLE III

| Ex. No. | m | R² | R¹ | R |
|---|---|---|---|---|
| | Column I<br>Br⁻(C₆H₅)₃P⁺—(CH₂)ₘ—COOH | Column II<br>R²Br/R²OMes | Column III<br>R¹ONH₂.HCl | Column IV<br>ROH |
| 74. | 3 | C₂H₅ | C₃H₇ | C₆H₅ |
| 75. | 4 | CH₂CH₂C₆H₅ | C₄H₉ | CH₂—C₆H₅ |
| 76. | 4 | —CH₂C₆H₅C | C₆H₅ | C₃H₇ |
| 77. | 1 | cyclohexyl | C₆H₅CH₂ | —CH₂—CH=CH₂ |

TABLE III-continued

| Ex. No. | m | R² | R¹ | R |
|---------|---|-----|-----|---|
| 78. | 4 | —CH₂—(cyclohexyl) | (cyclohexyl) | C₇H₁₅ |
| 79. | 5 | —CH₂—CH=CH—CH₃ | CH₃ | 2-pyridyl-CH₂— |
| 80. | 6 | —CH₂C≡CCH₂CH₃ | C₆H₅ | CH₃ |
| 81. | 4 | —CH(CH₃)—(phenyl) | (cyclopentyl)-CH₂— | —CH=CH₂ |
| 82. | 5 | —(4-hydroxyphenyl) | C₅H₁₁ | C₄H₉ |
| 83. | 6 | C₈H₁₇ | C₂H₅ | C₆H₅ |
| 84. | 7 | —(CH₂)₂C₆H₅ | C₇H₁₅ | 4-pyridyl-CH₂— |
| 85. | 8 | (cyclopentyl) | CH₃ | (CH₂)₂—C₆H₅ |

Column V $$\text{(norbornyl-O)} \begin{array}{c} CH_2-CH=CH-(CH_2)_m-\overset{OR}{\underset{|}{C}}=N-OR^1 \\ CH_2-O-R^2 \end{array}$$

| Ex. No. | | | | |
|---------|---|---|---|---|
| 74. | | | | |
| 75. | as in Column I | as in Column II | as in Column III | as in Column IV |
| 76. | | | | |
| 77. | | | | |
| 78. | | | | |
| 79. | | | | |
| 80. | | | | |
| 81. | | | | |
| 82. | | | | |
| 83. | | | | |
| 84. | | | | |
| 85. | | | | |

EXAMPLES 86 TO 97

Following the procedure of Examples 1, 9 and 17 and optionally 16 except replacing the 4-carboxybutyl triphenylphosphonium bromide with the compound shown in Column I, replacing 1-hexanethiol in Example 17 Part B with the compound shown in Column II of Table IV set out below and in Example 9 replacing O-benzylhydroxylamine hydrochloride with the compound shown in Column III (R¹ONH₂•HCl) and replacing phenethyl alcohol with the compound shown in Compound IV (ROH), the product shown in Column V is obtained wherein A is —CH=CH— where Example 16 is not followed, and A is (CH₂)₂ where Example 16 is followed.

TABLE IV

| Ex. No. | m | R² | R¹ | R |
|---------|---|-----|-----|---|
| | Column I<br>Br⁻(C₆H₅)₃P⁺—(CH₂)ₘ—COOH | Column II<br>R²SH | Column III<br>R¹ONH₂.HCl | Column IV<br>ROH |

TABLE IV-continued

| Ex. No. | m | R² | R¹ | R |
|---|---|---|---|---|
| 86. | 3 | C₂H₅ | C₃H₇ | C₆H₅ |
| 87. | 4 | C₆H₅ | C₄H₉ | CH₂—C₆H₅ |
| 88. | 4 | —CH₂C₆H₅ | C₆H₅ | C₃H₇ |
| 89. | 1 | ⬡ (cyclohexyl) | C₆H₅CH₂ | —CH₂—CH=CH₂ |
| 90. | 4 | —CH₂—⬡ (cyclohexylmethyl) | ⬡ (cyclohexyl) | C₇H₁₅ |
| 91. | 5 | —CH₂—CH=CH—CH₃ | CH₃ | pyridin-2-yl—C₂H₄— |
| 92. | 6 | —CH₂C≡CCH₂CH₃ | C₆H₅ | CH₃ |
| 93. | 4 | —CH(CH₃)—⬡ (1-cyclohexylethyl) | cyclopentyl—CH₂— | —CH=CH₂ |
| 94. | 5 | —C₆H₄—OH (4-hydroxyphenyl) | C₅H₁₁ | C₄H₉ |
| 95. | 6 | C₈H₁₇ | C₂H₅ | C₆H₅ |
| 96. | 7 | —(CH₂)₂C₆H₅ | C₇H₁₅ | C₃H₇ |
| 97. | 8 | cyclopentyl | CH₃ | (CH₂)₂—C₆H₅ |

Column V

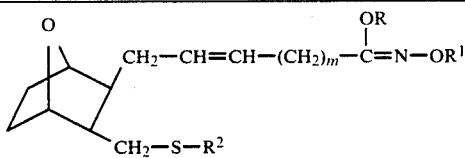

$$\text{norbornyl-CH}_2\text{—CH=CH—(CH}_2)_m\text{—C(OR)=N—OR}^1$$
$$\text{with CH}_2\text{—S—R}^2$$

| | | | | |
|---|---|---|---|---|
| 86. | | | | |
| 87. | as in | as in | as in | as in |
| 88. | Column I | Column II | Column III | Column IV |
| 89. | | | | |
| 90. | | | | |
| 91. | | | | |
| 92. | | | | |
| 93. | | | | |
| 94. | | | | |
| 95. | | | | |
| 96. | | | | |
| 97. | | | | |

EXAMPLES 98 TO 109

Following the procedure of Example 1 or 9 wherein Y is to be O or Example 17 wherein Y is to be S except replacing the 4-carboxybutyl triphenylphosphonium bromide with the compound shown in Column I, replacing hexylmesylate in Example 1 Part G or 1-hexanethiol in Example 17 with the compound shown in Column II of Table V set out below and replacing benzyl bromide in Example 1 Part O with the halide shown in Column III or phenethyl alcohol in Example 9 with the alcohol shown in Column III, the product shown in Column IV is obtained (wherein A is CH=CH).

TABLE V

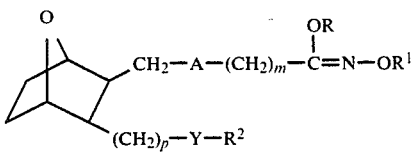

| Ex. No. | Column I<br>$Br^-(C_6H_5)_3P^+-(CH_2)_m-COOH$<br>m | Column II<br>$R^2Br$ or $R^2SH$<br>$YR^2$<br>$OR^2$ or $SR^2$ | Column HBr/<br>R—OH<br>R | Column IV m | $-OR^2$ or $-SR^2$ | R |
|---|---|---|---|---|---|---|
| 98. | 3 | $-SC_2H_5$ | $C_4H_9$ | | | |
| 99. | 10 | $-SC_6H_5$ | $C_2H_5$ | as in Column I | as in Column II | as in Column III |
| 100. | 4 | $-O-CH_2C_6H_5$ | $C_3H_7$ | | | |
| 101. | 3 | 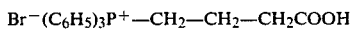 (—S—cyclohexyl) | $C_6H_5$ | | | |
| 102. | 1 | 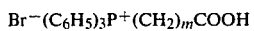 (—S—CH₂—cyclohexyl) | $CH_2-C_6H_5$ | | | |
| 103. | 4 | $-O-CH_2-CH=CH-CH_3$ | (pyridyl-CH₂—) | | | |
| 104. | 3 | $-S-CH_2C\equiv CCH_2CH_3$ | $CH_2-CH=CH_2$ | | | |
| 105. | 9 | $-S-CH(CH_3)-C_6H_5$ | $-CH_2-CH=CH_2$ | | | |
| 106. | 5 | $-O-C_6H_4-OH$ | $C_4H_9$ | | | |
| 107. | 6 | $-S-C_8H_{17}$ | $C_6H_5$ | | | |
| 108. | 7 | $-O-(CH_2)_2C_6H_5$ | $C_3H_7$ | | | |
| 109. | 8 | —S—(cyclopentyl) | $(CH_2)_2-C_6H_5$ | | | |

It will also be appreciated that the carboxybutyl triphenylphosphonium bromide of the structure $$Br^-(C_6H_5)_3P^+-CH_2-CH_2-CH_2COOH$$

employed in forming the upper side chain in the aforementioned examples may be replaced by $$Br^-(C_6H_5)_3P^+(CH_2)_mCOOH$$

wherein $(CH_2)_m$ is defined hereinbefore, to form compounds of the invention wherein the upper side chain is of the structure

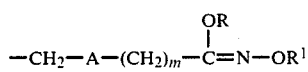

What is claimed is:
1. A compound of the structure

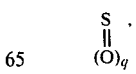

including all stereoisomers thereof, wherein A is —CH=CH— or —(CH₂)₂—; m is 0 to 10; R is lower alkyl, aryl, aralkyl or lower alkenyl containing 2 to 12 carbons; $R^1$ is H, lower alkyl, aryl, aralkyl, lower alkenyl containing 2 to 12 carbons, cycoalkyl, alkanoyl or aroyl; p is 1 to 5; Y is O or $$\underset{(O)_q}{\overset{S}{\|}}$$

wherein q is 0, 1 or 2; and $R^2$ is lower alkyl, aryl, arylalkyl, cycloalkyl, cycloalkylalkyl, lower alkenyl containing 2 to 12 carbons or lower alkynyl containing 2 to 12 carbons, or a pharmaceutically acceptable salt thereof, wherein lower alkyl or alkyl alone or as part of another group contains 1 to 12 carbons and is unsubstituted or is substituted with halo, $CF_3$, alkoxy, aryl, 2-, 3-, or 4-pyridyl, alkyl-aryl, haloaryl, cycloalkyl, or alkylcycloalkyl;

aryl alone or as part of another group represents phenyl or naphthyl and is unsubstituted or is substituted with 1 or 2 lower alkyl groups, 1 or 2 halogens, 1 or 2 hydroxy groups and/or 1 or 2 lower alkoxy groups;

cycloalkyl alone or as part of another group contains 3 to 12 carbons and is unsubstituted or is substituted with 1 or 2 halogens, 1 or 2 lower alkyl groups and/or 1 or 2 lower alkoxy groups;

$(CH_2)_m$ and $(CH_2)_p$ may contain 1 or 2 lower alkyl and/or 1 or 2 halo substituents.

2. The compound as defined in claim 1 wherein A is —CH=CH.

3. The compound as defined in claim 1 wherein A is —$(CH_2)_2$—.

4. The compound as defined in claim 1 wherein p is 1.

5. The compound as defined in claim 1 wherein m is 1 or 3.

6. The compound as defined in claim 1 wherein Y is O.

7. The compound as defined in claim 1 wherein Y is S.

8. The compound as defined in claim 6 wherein A is $CH_2$—$CH_2$ or CH=CH, m is 1 or 3, X is O, $R^1$ is H and R is lower alkyl, benzyl, p-fluoro- or o-fluorobenzyl, p is 1, Y is S and $R^2$ is lower alkyl, phenyl or benzyl.

9. The compound as defined in claim 1 wherein $R^2$ is butyl, pentyl, hexyl or heptyl including all isomers thereof.

10. The compound as defined in claim 1 [1R-[1α,2β(5Z),3β,4α]]-7-[3-[(hexyloxy)methyl]-7-oxabicyclo[2.2.1]hept-2-yl]-N-hydroxy-2,2-dimethyl-5-heptenimidic acid, phenylmethyl ester, including all stereoisomers thereof.

11. The compound as defined in claim 1 having the name [1R-[1α,2β(5Z),3β,4α]]-N-[7-[3-[(hexyloxy)methyl]-7-oxabicyclo[2.2.1]hept-2-yl]-1-methoxy-2,2-dimethyl-5-heptenylidene]hydroxylamine, including all stereoisomers thereof.

12. The compound as defined in claim 1 having the name [1R-[1α,2β(5Z),3β,4α]]-N-[7-[3-[(hexyloxy)methyl]-7-oxabicyclo[2.2.1]hept-2-yl]-2,2-dimethyl-1-propoxy-5-heptenylidene]hydroxylamine, including all stereoisomers thereof.

13. The compound as defined in claim 1 having the name [1R-[1α,2β(5Z),3β,4α]]-7-[3-[(hexyloxy)methyl]-7-oxabicyclo[2.2.1]hept-2-yl]-N-hydroxy-2,2-dimethyl-5-heptenimidic acid, 1-methylethyl ester or hexyl ester or dodecyl ester, including all stereoisomers thereof.

14. The compound as defined in claim 1 having the name [1R-[1α,2β(5Z),3β,4α]]-5-[3-[(hexyloxy)methyl]-7-oxabicyclo[2.2.1]hept-2-yl]-N-hydroxy-3-pentenimidic acid, phenylmethyl ester, including all stereoisomers thereof.

15. The compound as defined in claim 1 having the name [1R-[1α,2β(5Z),3β,4α]]-6-[3-[(hexyloxy)methyl]-7-oxabicyclo[2.2.1]hept-2-yl]-N-hydroxy-4-hexenimidic acid, phenylmethyl ester, including all stereoisomers thereof.

16. The compound as defined in claim 1 having the name [1R-[1α,2β(5Z),3β,4α]]-7-[3-[(hexyloxy)methyl]-7-oxabicyclo[2.2.1]hept-2-yl]-2,2-dimethyl-N-(phenylmethoxy)-5-heptenimidic acid, phenylmethyl ester or 2-phenylethyl ester, including all stereoisomers thereof.

17. The compund as defined in claim 1 having the name [1R-[1α,2β(5Z),3β,4α]]-7-[3-[(hexyloxy)methyl]-7-oxabicyclo[2.2.1]hept-2-yl]-N-hydroxy-2,2-dimethyl-5-heptenimidic acid, phenyl ester, 2-propenyl ester, (4-fluorophenyl)methyl ester, cyclohexyl ester, (4-methoxyphenyl)methyl ester or (2-fluorophenyl)methyl ester, including all stereoisomers thereof.

18. The compound as defined in claim 1 having the name [1R-[1α,2β(5Z),3β,4α]-7-[3-[(hexyloxy)methyl]-7-oxabicyclo[2.2.1]hept-2-yl]-N-methoxy-2,2-dimethyl-5-hepteneimidic acid, phenylmethyl ester.

19. The compound as defined in claim 1 having the name [1R-[1α,2β(Z),3β,4α]-7-[3-[(hexyloxy)methyl]-7-oxabicyclo[2.2.1]hept-2-yl]-N-hydroxy-2,2-dimethyl-5-heptenimidic acid, 2-propenyl ester, including all stereoisomers thereof.

20. A composition for inhibiting allergic conditions in a mammalian species, comprising an effective amount of a compound as defined in claim 1 or a pharmaceutically acceptable salt thereof, and a pharmaceutically acceptable carrier thereof.

21. A method of inhibiting $\Delta^5$-lipoxygenase which comprises administering to the circulatory system of a mammalian host an effective amount of a compound as defined in claim 1 or a pharmaceutically acceptable salt thereof.

22. The method as defined in claim 21 wherein said compound is administered in an amount within the range of from about 1 to about 100 mg/kg.

23. A method for treating asthma in a mammalian species in need of such treatment, which comprises administering to a mammalian host an effective amount of a compound as defined in claim 1.

24. A method of inhibiting cyclooxygenase or inhibiting or reducing inflammation, or inhibiting psoriasis or treating sunburn, which comprises systemically or topically administering to a mammalian host an effective amount of a compound as defined in claim 1.

* * * * *

UNITED STATES PATENT AND TRADEMARK OFFICE
CERTIFICATE OF CORRECTION

PATENT NO. : 4,673,685

DATED : June 16, 1987

INVENTOR(S) : Ravi K. Varma et al.

It is certified that error appears in the above-identified patent and that said Letters Patent is hereby corrected as shown below:

Title page, in the title, and Column 1, in the title, please change the title to read --Hydroximic Acids of 7-Oxabicycloheptane Substituted Ethers and Thioethers Useful in the Treatment of Inflammatory Disease--.

Signed and Sealed this

Thirteenth Day of October, 1987

Attest:

DONALD J. QUIGG

Attesting Officer

Commissioner of Patents and Trademarks